(12) United States Patent
Bierman et al.

(10) Patent No.: US 11,813,407 B2
(45) Date of Patent: Nov. 14, 2023

(54) ANCHORING SYSTEM FOR A CATHETER

(71) Applicant: C. R. Bard, Inc., Franklin Lakes, NJ (US)

(72) Inventors: Steven F. Bierman, Del Mar, CA (US); Richard A. Pluth, San Diego, CA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 670 days.

(21) Appl. No.: 16/783,009

(22) Filed: Feb. 5, 2020

(65) Prior Publication Data

US 2020/0171273 A1 Jun. 4, 2020

Related U.S. Application Data

(63) Continuation of application No. 15/489,594, filed on Apr. 17, 2017, now Pat. No. 10,561,815, which is a (Continued)

(51) Int. Cl.
*A61M 25/00* (2006.01)
*A61M 25/02* (2006.01)
*A61M 25/01* (2006.01)

(52) U.S. Cl.
CPC ............ *A61M 25/00* (2013.01); *A61M 25/01* (2013.01); *A61M 25/02* (2013.01); (Continued)

(58) Field of Classification Search
CPC .......... A61M 25/02; A61M 2025/0253; A61M 2025/026; A61M 2025/028; A61M 2025/024; Y10S 128/26
See application file for complete search history.

(56) References Cited

U.S. PATENT DOCUMENTS 2,525,398 A 10/1950 Collins
2,553,961 A 12/1950 Rousseau et al.
(Continued)

FOREIGN PATENT DOCUMENTS

CA 995995 A1 8/1976
CA 2228747 A1 2/1997
(Continued)

OTHER PUBLICATIONS

U.S. Appl. No. 16/394,969 filed Apr. 25 2019 Non-Final Office Action dated Aug. 3, 2021.
(Continued)

*Primary Examiner* — Nilay J Shah
(74) *Attorney, Agent, or Firm* — Rutan & Tucker LLP

(57) ABSTRACT

An anchoring system secures a catheter to the body of a patient and arrests axial movement of the catheter without impairing fluid flow through the catheter. The anchoring system can include an anchor pad that adheres to the patient's skin and supports a retainer. The retainer can include interengaging structure that moves the retainer between an open and a closed position. When in the open position, the retainer can receive a portion of the catheter and be subsequently moved to the closed position. The interengaging structure can allow the retainer to receive catheters of various sizes. The retainer can include one or more retention mechanisms to further inhibit axial movement of the catheter relative to the retainer when the catheter is secured therein. The anchoring system can include a mount that allows the retainer to rotate relative to the anchor pad.

16 Claims, 19 Drawing Sheets

Related U.S. Application Data continuation of application No. 12/063,225, filed as application No. PCT/US2006/034203 on Aug. 31, 2006, now Pat. No. 9,642,987.

(60) Provisional application No. 60/713,004, filed on Aug. 31, 2005.

(52) U.S. Cl.
CPC .  *A61M 2025/024* (2013.01); *A61M 2025/026* (2013.01); *A61M 2025/028* (2013.01); *A61M 2025/0246* (2013.01); *A61M 2025/0253* (2013.01); *A61M 2025/0266* (2013.01); *Y10S 128/26* (2013.01)

(56) References Cited

U.S. PATENT DOCUMENTS

| | | | |
|---|---|---|---|
| 2,707,953 | A | 5/1955 | Ryan |
| 2,893,671 | A | 7/1959 | Flora et al. |
| 3,046,984 | A | 7/1962 | Eby |
| 3,059,645 | A | 10/1962 | Hasbrouck et al. |
| 3,064,648 | A | 11/1962 | Bujan |
| 3,167,072 | A | 1/1965 | Stone et al. |
| 3,204,636 | A | 9/1965 | Kariher et al. |
| 3,256,880 | A | 6/1966 | Caypinar |
| 3,289,671 | A | 12/1966 | Troutman et al. |
| 3,471,109 | A | 10/1969 | Meyer |
| 3,482,569 | A | 12/1969 | Raaelli, Sr. |
| 3,524,443 | A | 8/1970 | Batlin |
| 3,526,880 | A | 9/1970 | Caypinar |
| 3,529,597 | A | 9/1970 | Fuzak |
| 3,542,321 | A | 11/1970 | Kahabka |
| 3,556,096 | A | 1/1971 | Fuller et al. |
| 3,602,227 | A | 8/1971 | Andrew |
| 3,630,195 | A | 12/1971 | Santomieri |
| 3,632,071 | A | 1/1972 | Cameron et al. |
| 3,677,250 | A | 7/1972 | Thomas |
| 3,700,574 | A | 10/1972 | Kehr |
| 3,731,684 | A | 5/1973 | Spiegel |
| 3,766,915 | A | 10/1973 | Rychlik |
| 3,834,380 | A | 9/1974 | Boyd |
| 3,847,370 | A | 11/1974 | Engelsher |
| 3,856,020 | A | 12/1974 | Kovac |
| 3,896,527 | A | 7/1975 | Miller et al. |
| 3,900,026 | A | 8/1975 | Wagner |
| 3,906,946 | A | 9/1975 | Nordstrom |
| 3,942,228 | A | 3/1976 | Buckman et al. |
| 3,942,750 | A | 3/1976 | Noorily |
| 3,973,565 | A | 8/1976 | Steer |
| 3,973,656 | A | 8/1976 | Zumbro |
| 3,993,081 | A | 11/1976 | Cussell |
| 4,020,835 | A | 5/1977 | Nordstrom et al. |
| 4,030,540 | A | 6/1977 | Roma |
| 4,057,066 | A | 11/1977 | Taylor |
| 4,059,105 | A | 11/1977 | Cutruzzula et al. |
| 4,082,094 | A | 4/1978 | Dailey |
| 4,114,618 | A | 9/1978 | Margas |
| 4,114,626 | A | 9/1978 | Beran |
| 4,129,128 | A | 12/1978 | McFarlane |
| 4,133,307 | A | 1/1979 | Ness |
| 4,142,527 | A | 3/1979 | Garcia |
| 4,149,539 | A | 4/1979 | Cianci |
| 4,161,177 | A | 7/1979 | Fuchs |
| 4,170,995 | A * | 10/1979 | Levine .................. A61M 25/02 24/304 |
| 4,193,174 | A | 3/1980 | Stephens |
| 4,224,937 | A | 9/1980 | Gordon |
| 4,248,229 | A | 2/1981 | Miller |
| 4,250,880 | A | 2/1981 | Gordon |
| 4,316,461 | A | 2/1982 | Marais et al. |
| 4,324,236 | A | 4/1982 | Gordon et al. |
| 4,326,519 | A | 4/1982 | D'Alo et al. |
| 4,333,468 | A | 6/1982 | Geist |
| 4,353,369 | A | 10/1982 | Muetterties et al. |
| 4,356,599 | A | 11/1982 | Larson et al. |
| 4,362,156 | A | 12/1982 | Feller, Jr. et al. |
| 4,389,754 | A | 6/1983 | Sohma |
| 4,392,853 | A | 7/1983 | Muto |
| 4,392,857 | A | 7/1983 | Beran |
| 4,397,647 | A | 8/1983 | Gordon |
| 4,405,163 | A | 9/1983 | Voges et al. |
| 4,442,994 | A | 4/1984 | Logsdon |
| 4,449,975 | A | 5/1984 | Perry |
| 4,453,933 | A | 6/1984 | Speaker |
| 4,474,559 | A | 10/1984 | Steiger |
| 4,480,639 | A | 11/1984 | Peterson et al. |
| 4,484,913 | A | 11/1984 | Swauger |
| 4,490,141 | A | 12/1984 | Lacko et al. |
| 4,498,903 | A | 2/1985 | Mathew |
| 4,500,338 | A | 2/1985 | Young et al. |
| 4,502,477 | A | 3/1985 | Lewis |
| 4,516,293 | A | 5/1985 | Beran |
| 4,516,968 | A | 5/1985 | Marshall et al. |
| 4,517,971 | A | 5/1985 | Sorbonne |
| 4,533,349 | A | 8/1985 | Bark |
| 4,534,762 | A | 8/1985 | Heyer |
| 4,563,177 | A | 1/1986 | Kamen |
| 4,579,120 | A | 4/1986 | MacGregor |
| 4,583,976 | A | 4/1986 | Ferguson |
| 4,589,702 | A * | 5/1986 | Bach .................. A63H 33/042 301/64.704 |
| 4,617,017 | A | 10/1986 | Hubbard et al. |
| 4,621,029 | A | 11/1986 | Kawaguchi |
| 4,623,102 | A | 11/1986 | Hough, Jr. |
| 4,633,863 | A | 1/1987 | Filips et al. |
| 4,636,552 | A | 1/1987 | Gay et al. |
| 4,650,473 | A | 3/1987 | Bartholomew et al. |
| 4,659,329 | A | 4/1987 | Annis |
| 4,660,555 | A | 4/1987 | Payton |
| 4,661,110 | A * | 4/1987 | Fortier .................. A61M 39/20 604/905 |
| 4,669,156 | A | 6/1987 | Guido et al. |
| 4,699,616 | A | 10/1987 | Nowak et al. |
| 4,711,636 | A | 12/1987 | Bierman |
| D293,717 | S | 1/1988 | Proulx et al. |
| 4,726,716 | A | 2/1988 | McGuire |
| 4,733,666 | A | 3/1988 | Mercer, Jr. |
| 4,737,143 | A | 4/1988 | Russell |
| 4,742,824 | A | 5/1988 | Payton et al. |
| 4,762,513 | A | 8/1988 | Choy et al. |
| 4,775,121 | A | 10/1988 | Carty |
| 4,808,162 | A | 2/1989 | Oliver |
| 4,823,789 | A | 4/1989 | Beisang, III |
| 4,826,486 | A | 5/1989 | Palsrok et al. |
| 4,828,549 | A | 5/1989 | Kvalo |
| 4,838,878 | A | 6/1989 | Kalt et al. |
| 4,852,844 | A | 8/1989 | Villaveces |
| 4,857,058 | A | 8/1989 | Payton Hugh W. |
| 4,863,432 | A | 9/1989 | Kvalo |
| 4,869,465 | A | 9/1989 | Yirmiyahu et al. |
| 4,874,380 | A * | 10/1989 | Hesketh ................. A61M 25/02 604/338 |
| 4,880,412 | A | 11/1989 | Weiss |
| 4,881,705 | A | 11/1989 | Kraus |
| 4,896,465 | A | 1/1990 | Rhodes et al. |
| 4,897,082 | A | 1/1990 | Erskine |
| 4,898,587 | A | 2/1990 | Mera |
| 4,899,963 | A | 2/1990 | Murphy |
| 4,919,654 | A | 4/1990 | Kalt |
| D308,576 | S | 6/1990 | Iversen |
| 4,932,943 | A | 6/1990 | Nowak |
| 4,944,728 | A | 7/1990 | Carrell et al. |
| 4,952,207 | A | 8/1990 | Lemieux |
| 4,955,864 | A | 9/1990 | Hajduch |
| 4,976,700 | A | 12/1990 | Tollini |
| 4,997,421 | A | 3/1991 | Palsrok et al. |
| 5,000,741 | A | 3/1991 | Kalt |
| 5,037,397 | A | 8/1991 | Kalt et al. |
| 5,073,166 | A | 12/1991 | Parks et al. |
| 5,073,170 | A | 12/1991 | Schneider |
| 5,078,731 | A | 1/1992 | Hayhurst |
| 5,084,026 | A | 1/1992 | Shapiro |
| 5,098,399 | A | 3/1992 | Tollini |

(56) References Cited

U.S. PATENT DOCUMENTS

| | | | |
|---|---|---|---|
| 5,112,313 A | 5/1992 | Sallee | |
| 5,147,322 A | 9/1992 | Bowen et al. | |
| 5,156,641 A | 10/1992 | White | |
| 5,163,914 A | 11/1992 | Abel | |
| 5,188,609 A * | 2/1993 | Bayless | F16L 3/137 |
| | | | 604/174 |
| 5,192,273 A | 3/1993 | Bierman | |
| 5,192,274 A | 3/1993 | Bierman | |
| 5,195,981 A | 3/1993 | Johnson | |
| 5,224,935 A | 7/1993 | Hollands | |
| 5,226,892 A | 7/1993 | Boswell | |
| 5,234,185 A | 8/1993 | Hoffman et al. | |
| 5,250,041 A | 10/1993 | Folden et al. | |
| 5,257,768 A | 11/1993 | Juenemann et al. | |
| 5,263,939 A * | 11/1993 | Wortrich | A61B 17/34 |
| | | | 604/174 |
| 5,263,943 A | 11/1993 | Vanderbrook | |
| 5,266,401 A | 11/1993 | Tollini | |
| 5,267,967 A | 12/1993 | Schneider | |
| 5,280,866 A | 1/1994 | Ueki | |
| 5,282,463 A | 2/1994 | Hammersley | |
| 5,290,248 A | 3/1994 | Bierman et al. | |
| 5,292,312 A | 3/1994 | Delk et al. | |
| 5,304,146 A | 4/1994 | Johnson et al. | |
| 5,306,243 A | 4/1994 | Bonaldo | |
| D347,060 S | 5/1994 | Bierman | |
| 5,308,337 A | 5/1994 | Bingisser | |
| 5,314,411 A | 5/1994 | Bierman et al. | |
| 5,318,546 A | 6/1994 | Bierman | |
| 5,322,514 A | 6/1994 | Steube et al. | |
| 5,330,438 A | 7/1994 | Gollobin et al. | |
| 5,334,186 A | 8/1994 | Alexander | |
| 5,336,195 A | 8/1994 | Daneshvar | |
| 5,338,308 A | 8/1994 | Wilk | |
| 5,342,317 A | 8/1994 | Claywell | |
| 5,344,406 A | 9/1994 | Spooner | |
| 5,344,414 A | 9/1994 | Lopez et al. | |
| 5,345,931 A | 9/1994 | Battaglia, Jr. | |
| 5,346,479 A | 9/1994 | Schneider | |
| 5,352,211 A | 10/1994 | Merskelly | |
| 5,354,282 A | 10/1994 | Bierman | |
| 5,354,283 A | 10/1994 | Bark et al. | |
| 5,368,575 A | 11/1994 | Chang | |
| 5,374,254 A | 12/1994 | Buma | |
| 5,380,293 A | 1/1995 | Grant | |
| 5,380,294 A | 1/1995 | Persson | |
| 5,380,301 A | 1/1995 | Prichard et al. | |
| 5,382,239 A | 1/1995 | Orr et al. | |
| 5,382,240 A | 1/1995 | Lam | |
| 5,389,082 A | 2/1995 | Baugues et al. | |
| 5,395,344 A | 3/1995 | Beisang, III et al. | |
| 5,397,639 A | 3/1995 | Tollini | |
| 5,398,679 A | 3/1995 | Freed | |
| 5,403,285 A | 4/1995 | Roberts | |
| 5,413,562 A | 5/1995 | Swauger | |
| 5,443,460 A | 8/1995 | Miklusek | |
| 5,449,349 A | 9/1995 | Sallee et al. | |
| 5,456,671 A | 10/1995 | Bierman | |
| 5,468,228 A | 11/1995 | Gebert | |
| 5,468,230 A | 11/1995 | Corn | |
| 5,468,231 A | 11/1995 | Newman et al. | |
| 5,470,321 A | 11/1995 | Forster et al. | |
| D364,922 S | 12/1995 | Bierman | |
| 5,474,572 A | 12/1995 | Hayhurst | |
| 5,484,420 A | 1/1996 | Russo | |
| 5,494,245 A | 2/1996 | Suzuki et al. | |
| 5,496,282 A | 3/1996 | Militzer et al. | |
| 5,496,283 A | 3/1996 | Alexander | |
| 5,499,976 A | 3/1996 | Dalton | |
| 5,520,656 A | 5/1996 | Byrd | |
| 5,522,803 A | 6/1996 | Teissen-Simony | |
| 5,527,293 A | 6/1996 | Zamierowski | |
| 5,539,020 A | 7/1996 | Bracken et al. | |
| 5,549,567 A | 8/1996 | Wolman | |
| 5,551,421 A | 9/1996 | Noureldin et al. | |
| D375,355 S | 11/1996 | Bierman | |
| D375,356 S | 11/1996 | Bierman | |
| 5,578,013 A | 11/1996 | Bierman | |
| D377,831 S | 2/1997 | Bierman | |
| 5,613,655 A | 3/1997 | Marion | |
| 5,616,135 A | 4/1997 | Thorne et al. | |
| 5,626,565 A | 5/1997 | Landis et al. | |
| 5,632,274 A | 5/1997 | Quedens et al. | |
| 5,637,098 A | 6/1997 | Bierman | |
| 5,643,217 A | 7/1997 | Dobkin | |
| 5,653,411 A | 8/1997 | Picco et al. | |
| 5,672,159 A | 9/1997 | Warrick | |
| 5,676,137 A | 10/1997 | Byrd | |
| 5,681,290 A | 10/1997 | Alexander | |
| 5,685,859 A | 11/1997 | Kornerup | |
| 5,690,617 A | 11/1997 | Wright | |
| 5,693,032 A | 12/1997 | Bierman | |
| 5,697,907 A | 12/1997 | Gaba | |
| 5,702,371 A | 12/1997 | Bierman | |
| D389,911 S | 1/1998 | Bierman | |
| 5,722,959 A | 3/1998 | Bierman | |
| D393,903 S | 4/1998 | Bierman | |
| 5,738,660 A | 4/1998 | Luther | |
| 5,755,225 A * | 5/1998 | Hutson | A61M 16/0488 |
| | | | 128/207.14 |
| 5,776,106 A | 7/1998 | Matyas | |
| 5,785,201 A | 7/1998 | Bordner et al. | |
| 5,795,335 A | 8/1998 | Zinreich | |
| 5,800,402 A | 9/1998 | Bierman | |
| 5,810,781 A * | 9/1998 | Bierman | A61M 25/02 |
| | | | 604/174 |
| D399,954 S | 10/1998 | Bierman | |
| 5,827,230 A | 10/1998 | Bierman | |
| 5,827,239 A | 10/1998 | Dillon et al. | |
| D401,329 S | 11/1998 | Bierman | |
| 5,833,663 A | 11/1998 | Bierman et al. | |
| 5,846,255 A | 12/1998 | Casey | |
| D404,815 S | 1/1999 | Bierman | |
| 5,855,591 A | 1/1999 | Bierman | |
| 5,916,199 A | 6/1999 | Miles | |
| 5,921,991 A | 7/1999 | Whitehead et al. | |
| 5,922,470 A | 7/1999 | Bracken et al. | |
| 5,941,263 A | 8/1999 | Bierman | |
| 5,944,696 A * | 8/1999 | Bayless | A61M 25/02 |
| | | | 604/174 |
| 6,001,081 A | 12/1999 | Collen | |
| 6,015,119 A | 1/2000 | Starchevich | |
| 6,024,761 A | 2/2000 | Barone et al. | |
| 6,027,480 A | 2/2000 | Davis et al. | |
| 6,054,523 A | 4/2000 | Braun et al. | |
| D425,619 S | 5/2000 | Bierman | |
| 6,074,368 A | 6/2000 | Wright | |
| 6,113,577 A | 9/2000 | Hakky et al. | |
| 6,117,163 A | 9/2000 | Bierman | |
| 6,131,575 A | 10/2000 | Lenker et al. | |
| 6,132,398 A | 10/2000 | Bierman | |
| 6,132,399 A | 10/2000 | Shultz | |
| 6,206,897 B1 | 3/2001 | Jamiolkowski et al. | |
| 6,213,979 B1 | 4/2001 | Bierman | |
| 6,224,571 B1 | 5/2001 | Bierman | |
| 6,228,064 B1 | 5/2001 | Abita et al. | |
| 6,231,548 B1 | 5/2001 | Bassett | |
| 6,258,066 B1 | 7/2001 | Urich | |
| 6,273,873 B1 | 8/2001 | Fleischer | |
| 6,274,786 B1 | 8/2001 | Heller | |
| 6,283,945 B1 | 9/2001 | Bierman | |
| 6,290,676 B1 | 9/2001 | Bierman | |
| 6,332,874 B1 | 12/2001 | Eliasen et al. | |
| 6,361,523 B1 | 3/2002 | Bierman | |
| 6,387,075 B1 | 5/2002 | Stivland et al. | |
| 6,387,076 B1 | 5/2002 | Landuyt | |
| 6,413,240 B1 | 7/2002 | Bierman et al. | |
| 6,419,660 B1 | 7/2002 | Russo | |
| 6,428,514 B1 * | 8/2002 | Goebel | A61M 39/1055 |
| | | | 604/177 |
| 6,428,515 B1 | 8/2002 | Bierman et al. | |
| 6,447,485 B2 | 9/2002 | Bierman | |
| 6,458,104 B2 | 10/2002 | Gautsche | |
| 6,491,664 B2 | 12/2002 | Bierman | |

(56) References Cited

U.S. PATENT DOCUMENTS

| | | |
|---|---|---|
| 6,500,154 B1 | 12/2002 | Hakky et al. |
| D470,936 S | 2/2003 | Bierman |
| 6,551,285 B1 | 4/2003 | Bierman |
| 6,572,588 B1 | 6/2003 | Bierman et al. |
| 6,582,403 B1 | 6/2003 | Bierman et al. |
| 6,585,703 B1 | 7/2003 | Kassel et al. |
| 6,596,402 B2 | 7/2003 | Soerens et al. |
| D480,144 S | 9/2003 | Adams et al. |
| 6,663,600 B2 | 12/2003 | Bierman et al. |
| 6,685,670 B2 | 2/2004 | Miles et al. |
| 6,703,120 B1 | 3/2004 | Ko et al. |
| D492,411 S | 6/2004 | Bierman |
| 6,770,055 B2 | 8/2004 | Bierman et al. |
| 6,786,892 B2 | 9/2004 | Bierman |
| 6,796,310 B2 | 9/2004 | Bierman |
| 6,829,705 B2 | 12/2004 | Smith |
| 6,837,875 B1 | 1/2005 | Bierman |
| 6,872,194 B2 | 3/2005 | Doyle et al. |
| D503,977 S | 4/2005 | Bierman |
| 6,951,550 B2 | 10/2005 | Bierman |
| 6,984,145 B1 | 1/2006 | Lim |
| 7,018,362 B2 | 3/2006 | Bierman et al. |
| 7,074,208 B2 * | 7/2006 | Pajunk .................. A61M 25/02 128/DIG. 6 |
| 7,115,321 B2 | 10/2006 | Soerens et al. |
| 7,320,681 B2 | 1/2008 | Gillis et al. |
| 7,354,421 B2 | 4/2008 | Bierman |
| 7,879,013 B2 | 2/2011 | Smith et al. |
| 8,052,648 B2 | 11/2011 | Dikeman et al. |
| 8,394,067 B2 | 3/2013 | Bracken et al. |
| 8,915,885 B2 | 12/2014 | Smith et al. |
| 9,616,200 B2 | 4/2017 | Smith et al. |
| 9,642,987 B2 | 5/2017 | Bierman et al. |
| 10,322,262 B2 | 6/2019 | Bracken et al. |
| 10,561,815 B2 | 2/2020 | Bierman et al. |
| 2002/0026152 A1 * | 2/2002 | Bierman ............... A61M 25/02 604/174 |
| 2002/0095119 A1 | 7/2002 | Bertoch et al. |
| 2002/0161332 A1 | 10/2002 | Ramey |
| 2002/0165493 A1 | 11/2002 | Bierman |
| 2003/0125668 A1 | 7/2003 | Bierman |
| 2004/0167475 A1 | 8/2004 | Wright et al. |
| 2005/0137496 A1 | 6/2005 | Walsh et al. |
| 2005/0192539 A1 | 9/2005 | Bierman et al. |
| 2005/0205708 A1 | 9/2005 | Sasaki et al. |
| 2005/0282977 A1 | 12/2005 | Stempel et al. |
| 2006/0025723 A1 | 2/2006 | Ballarini |
| 2006/0129103 A1 | 6/2006 | Bierman et al. |
| 2006/0233652 A1 | 10/2006 | Kim et al. |
| 2006/0289011 A1 | 12/2006 | Helsel |
| 2007/0032561 A1 | 2/2007 | Lin et al. |
| 2007/0142782 A2 | 6/2007 | Bierman |
| 2007/0142784 A1 | 6/2007 | Dikeman et al. |
| 2007/0265572 A1 | 11/2007 | Smith et al. |
| 2007/0276335 A1 | 11/2007 | Bierman |
| 2008/0029476 A1 | 2/2008 | Ohmi et al. |
| 2008/0097334 A1 | 4/2008 | Dikeman et al. |
| 2008/0249476 A1 | 10/2008 | Bierman et al. |
| 2009/0137962 A1 | 5/2009 | Bracken et al. |
| 2009/0149814 A1 | 6/2009 | Bailey et al. |
| 2010/0100049 A1 | 4/2010 | Godfrey |
| 2010/0298778 A1 | 11/2010 | Bracken et al. |
| 2011/0060295 A1 | 3/2011 | Hen et al. |
| 2012/0271240 A1 | 10/2012 | Andino et al. |
| 2013/0150827 A1 | 6/2013 | Bracken et al. |
| 2015/0112270 A1 | 4/2015 | Smith et al. |
| 2015/0217088 A1 | 8/2015 | Zyzelewski et al. |
| 2015/0224285 A1 | 8/2015 | Howell et al. |
| 2016/0193452 A1 | 7/2016 | Hanson et al. |
| 2017/0216556 A1 | 8/2017 | Bierman et al. |
| 2018/0161543 A1 | 6/2018 | Burkholz |
| 2019/0247623 A1 | 8/2019 | Helm et al. |
| 2019/0247625 A1 | 8/2019 | Bracken et al. |
| 2020/0246592 A1 | 8/2020 | Clavijo et al. |

FOREIGN PATENT DOCUMENTS

| | | | |
|---|---|---|---|
| CA | 2208577 A1 | 5/1997 | |
| CA | 2306802 A1 | 4/1999 | |
| CA | 2310030 A1 | 5/1999 | |
| CA | 2281457 A1 | 2/2001 | |
| CA | 2402507 A1 | 9/2001 | |
| CA | 2418000 A1 | 2/2002 | |
| CA | 2483995 A1 | 4/2004 | |
| DE | 2341297 A1 | 4/1975 | |
| DE | 3110023 A1 | 9/1982 | |
| DE | 8811131 U1 | 1/1989 | |
| DE | 1000380 A1 | 8/1990 | |
| DE | 29608294 U1 | 8/1996 | |
| EP | 0064284 A2 | 11/1982 | |
| EP | 0247590 A2 | 12/1987 | |
| EP | 0274418 A2 | 7/1988 | |
| EP | 0356683 A1 | 3/1990 | |
| EP | 0440101 A2 | 8/1991 | |
| EP | 0470709 A1 | 2/1992 | |
| EP | 0597213 A1 | 5/1994 | |
| EP | 0931560 A1 | 7/1999 | |
| FR | 1184139 A | 7/1959 | |
| FR | 2381529 A1 | 9/1978 | |
| FR | 2722414 A1 | 1/1996 | |
| FR | 2852520 A1 | 9/2004 | |
| GB | 2063679 A | 6/1981 | |
| GB | 2086466 A | 5/1982 | |
| GB | 2219034 A | 11/1989 | |
| GB | 2233902 A | 1/1991 | |
| GB | 2288542 A | 10/1995 | |
| GB | 2312619 A | 11/1997 | |
| JP | 52-004691 B | 2/1977 | |
| JP | S60-051377 | 4/1985 | |
| JP | 63501477 | 6/1988 | |
| JP | 01308572 | 12/1989 | |
| JP | 1992-051767 | 3/1992 | |
| JP | H04-037448 | 3/1992 | |
| JP | 06-063153 | 3/1994 | |
| JP | 1995-028563 | 5/1995 | |
| JP | 08024344 | 1/1996 | |
| JP | H08-257138 A | 10/1996 | |
| NL | 1015663 C2 | 1/2002 | |
| NL | 1015663 C2 * | 1/2002 | ............ A61M 25/02 |
| WO | 8001458 A1 | 7/1980 | |
| WO | 8502774 A1 | 7/1985 | |
| WO | 86/06641 A1 | 11/1986 | |
| WO | 9116939 A1 | 11/1991 | |
| WO | 9219309 A1 | 11/1992 | |
| WO | 9610435 A1 | 4/1996 | |
| WO | 9626756 A1 | 9/1996 | |
| WO | 9853872 A1 | 12/1998 | |
| WO | 2015035238 A1 | 3/2015 | |
| WO | 2018/138324 A1 | 8/2018 | |

OTHER PUBLICATIONS

U.S. Appl. No. 16/777,714, filed Jan. 30, 2020 Non-Final Office Action dated Jul. 7, 2021.

Plaintiff's Opening Claim Construction Brief; *Venetec International Inc v. Nexus Medical, LLC*, U.S District Court for Delaware, Case No. 07-CV-0057***, Oct. 10, 2008.

Plaintiff's Answering Brief in Opposition to Defendant's Motion for Summary Judgement of invalidity; Filed: Oct. 30, 2008; *Venetec International, Inc., v. Nexus Medical, LLC*; USDC, District of Delaware, Civil Action No. 07-cv-0057-MPT. (Oct. 30, 2008).

Rebuttal Expert Report of Dr. Terry N. Layton, Ph D., *Venetec International Inc. v. Nexus Medical, LLC*, U.S. District Court for Delaware, Case No. 07-CV-0057***, Aug. 29, 2008, 33 pgs.

Request for Inter Partes Reexamination Under 37 C.F.R. 1.913 [filed Jun. 25, 2007] In re Bierman, USPTO, Reexamination No. 95/000,271.

Search Result, Percufix® Catheter Cuff Kit, downloaded from the Internet on Aug. 15, 2001.

Second Supplemental Complaint [filed Sep. 5, 2007]. *Venetec Int'l, Inc. v. Nexus Medical, LLC*, USDC D.Del., Case No. 1:07-CV-00057.

(56) References Cited

OTHER PUBLICATIONS

Stipulation and Order amending Nexus Medical, LLC's Answer to Complaint and Counterclaim, *Venetec International Inc.* v. *Nexus Medical, LLC,* U.S. District Court for Delaware, Case No. 07-CV-005, 15 pgs. (Jul. 13, 2007).
Third-Party Requester's Response to Patent Owner's Response to Office Action dated Sep. 21, 2007, Inter Partes Reexamination No. 95/000,271, Dec. 21, 2007, 85 pages.
Third-Party Requester's Supplemental Response to Patent Owner's Supplemental Response to Office Action dated Sep. 21, 2007, Inter Partes Reexamination No. 95/000,271, Jan. 22, 2008, 48 pgs.
Transcript of Claim Construction Hearing; *Venetec International Inc.* v. *Nexus Medical, LLC,* U.S. District Court for Delaware, Case No. 07-CV-0057***, Nov. 21, 2008.
Tri-State Hospital Supply Corporation, Centurion Healthcare Products brochure for HubGuard Catheter Securement (Mar. 3, 2004).
Tri-State Hospital Supply Corporation, Centurion Healthcare Products brochure for IV Start Kits (Sep. 14, 2004).
Tri-State Hospital Supply Corporation, Centurion Healthcare Products brochure for LineGuard J-Loop Securement Device (Nov. 2, 2004).
Tri-State Hospital Supply Corporation, Centurion Healthcare Products brochure for Port Access Trays (Apr. 24, 2003).
Tri-State Hospital Supply Corporation, Centurion Healthcare Products brochure for SorbaView 2000 Window Dressing (Apr. 14, 2004).
Tri-State Hospital Supply Corporation, Centurion Healthcare Products brochure for SorbaView Ultimate Window Dressing (May 7, 2004 and Jun. 22, 2004).
U.S. Appl. No. 12/063,225, filed Feb. 7, 2008 Final Office Action dated Jun. 21, 2016.
U.S. Appl. No. 12/063,225, filed Feb. 7, 2008 Non-Final Office Action dated Nov. 30, 2015.
U.S. Appl. No. 12/063,225, filed Feb. 7, 2008 Notice of Allowance dated Jan. 6, 2017.
U.S. Appl. No. 13/762,803, filed Feb. 8, 2013 Board Decision dated Jul. 3, 2018.
U.S. Appl. No. 13/762,803, filed Feb. 8, 2013 Non-Final Office Action dated Jul. 2, 2015.
U.S. Appl. No. 13/762,803, filed Feb. 8, 2013 Notice of Allowance dated Oct. 10, 2018.
U.S. Appl. No. 13/762,803, filed Feb. 8, 2013 Examiner's Answer dated Dec. 1, 2016.
U.S. Appl. No. 13/762,803, filed Feb. 8, 2013 Final Office Action dated Oct. 30, 2015.
U.S. Appl. No. 14/580,720, filed Dec. 23, 2014 Non-Final Office Action dated Sep. 9, 2016.
U.S. Appl. No. 15/489,594, filed Apr. 17, 2017 Advisory Action dated Jun. 12, 2019.
U.S. Appl. No. 15/489,594, filed Apr. 17, 2017 Final Office Action dated Mar. 7, 2019.
U.S. Appl. No. 15/489,594, filed Apr. 17, 2017 Non-Final Office Action dated Sep. 28, 2018.
U.S. Appl. No. 15/489,594, filed Apr. 17, 2017 Notice of Allowance dated Oct. 1, 2019.
U.S. Appl. No. 90/010,167, filed May 15, 2008 Decision by the Board of Patent Appeals and Interferences (BPSI) in the Ex Parte Reexamination of the '949 patent, dated Aug. 24, 2010.
U.S. Appl. No. 90/010,211, filed Jun. 27, 2008 Decision by the Board of Patent Appeals and Interferences (BPAI) in the Ex Parte Reexamination of the '150 patent, dated Sep. 7, 2010.
Venetec International, Inc.'s Reply to Nexus Medical, LLC's Counterclaim [filed Apr. 11, 2007]. *Venetec Int'l, Inc.* v. *Nexus Medical, LLC,* USDC D.Del., Case No. 1:07-CV-00057.
Venetec International, Inc.'s Reply to Nexus Medical, LLC's Counterclaim [filed Aug. 28, 2007]. *Venetec Int'l, Inc.* v. *Nexus Medical, LLC,* USDC D.Del., Case No. 1:07-CV-00057.
Venetec International, Inc.'s Reply to Nexus Medical, LLC's Counterclaim [filed Sep. 27, 2007]. *Venetec Int'l, Inc.* v. *Nexus Medical, LLC,* USDC D.Del., Case No. 1:07-CV-00057.

Venetec's letter to Judge Thynge dated Sep. 28, 2007, *Venetec International Inc.* v. *Nexus Medical, LLC,* U.S. District Court for Delaware, Case No. 07-CV-0057***, 6 pgs.
Venetec's Motion for Partial Judgement on the Pleadings, *Venetec International Inc.* v. *Nexus Medical, LLC,* U.S. District Court for Delaware, Case No. 07-CV-0057, 3 pgs (Sep. 28, 2007).
Venetec's Motion for Partial Judgement on the Pleadings, *Venetec International Inc.* v. *Nexus Medical, LLC,* U.S. District Court for Delaware, Case No. 07-CV-0057, 34 pgs. (Sep. 28, 2007).
Venetec's Opening Brief in Support of Motion for Partial Judgement on the Pleadings, *Venetec International Inc.* v. *Nexus Medical, LLC,* U.S. District Court for Delaware, Case No. 07-Cv-0057, 34 pgs. (Sep. 28, 2007).
Zefon International printout from www.zefon.com/medical/griplok.htm depicting prior art GRIP-LOK Universal Tubing Securement Device (printed Jun. 20, 2005).
U.S. Appl. No. 16/394,969, filed Apr. 25, 2019 Final Office Action dated Jan. 21, 2022.
U.S. Appl. No. 16/777,714, filed Jan. 30, 2020 Final Office Action dated Dec. 9, 2021.
"Occlude". Merriam-Webster Online Dictionary, <http://www.merriam-webster.com/dictionary/occlude>. Last accessed May 12, 2011.
3M Technical Data Sheet entitled "Adhesive Transfer Tapes with Adhesive 300MP 9692-9695-964" (Sep. 2002).
Bostick Findley Product Data Sheet entitled "4229 Hot Melt Adhesives" (Sep. 2003).
Brief in Support of Nexus Medical, LLC's Motion for Summary Judgement of Noninfringement of the Venetec Patents (Public Redacted Version); *Venetec International Inc.* v. *Nexus Medical, LLC,* U.S. District Court for Delaware, Case No. 07-CV-0057,Public version filed Oct. 24, 2008, 158 pgs.
Brief in Support of Nexus Medical, LLC's Motion for Summary Judgement that the Venetec Patents are Invalid; *Venetec International Inc.* v. *Nexus Medical, LLC,* USDC, District of Delaware, Civil Action No. 07-cv-0057-MPT. Dated Oct. 10, 2008.
CA 2,619,979 filed Aug. 31, 2006 Office Action dated Oct. 7, 2015.
Civil Docket for Case No. 1:07-CV-00057*** [printed Oct. 22, 2007].
Complaint [dated Jan. 29, 2007]. *Venetec Int'l, Inc.* v. *Nexus Medical, LLC,* USDC D.Del., Case No. 1:07-CV-00057.
Declaration of Jennifer C. Bailey in Support of Nexus' Opposition to Venetec's Motion for Partial Judgement on the Pleadings, *Venetec International Inc.* v. *Nexus Medical, LLC,* U.S. District Court for Delaware, Case No. 07-CV-0057, 31 pgs. cited byother (Mar. 15, 2007).
Defendant Nexus Medical, LLC's Objections and Responses to Plantiff Venetec International, Inc's Modified and Supplemental Definitions Set Forth in its First Set of interrogatories to Defendant *Nexus Medical, LLC, Venetec International Inc.* v. *NexusMedical, LLC,* U.S. District Court for Delaware, Case No. 07-Cv-0057, 79 pgs. (May 30, 2007).
Defendant Nexus Medical, LLC's Reply to Plantiff s Answering Brief in Opposition to Defendant's Motion for Summary Judgement of Invalidity; Filed: Nov. 10, 2008; *Venetec International Inc.* v. *Nexus Medical, LLC*; USDC, District of Delaware, CivilAction No. 07-cv-0057-MPT. (Nov. 10, 2008).
Defendant Nexus Medical, LLC's Reply to Plantiff's Answering Brief in Opposition to Defendant's Motion for Summary Judgement of Noninfringement of the Venetec Patents (Public Version); *Venetec International Inc.* v. *Nexus Medical, LLC,* U.S. DistrictCourt for Delaware, Case No. 07-CV-0057, Public version filed Nov. 18, 2008, 27 pgs.
EP 04 07 6329 European Search Report dated Feb. 7, 2005.
EP 06 802789 (PCT/US2006/034203) Supplementary Partial European Search Report dated May 15, 2009.
Expert Report of Julie E. Shomo Regarding Invalidity of the Venetec Patents Pursuant to Rule 26(a)(2)(B), *Venetec International Inc.* v. *Nexus Medical, LLC,* U.S. District Court for Delaware, Case No. 07-CV-0057***, Jul. 18, 2008, 31 pgs. cited byapplicant.
Expert Report of Marvin Gordon Regarding Invalidity of the Venetec Patents Pursuant to Rule 26(a)(2)(B), *Venetec International*

(56) References Cited

OTHER PUBLICATIONS

*Inc. v. Nexus Medical, LLC*, U.S. District Court for Delaware, Case No. 07-CV-0057***, Jul. 18, 2008, 23 pgs. cited byapplicant.

Expert Report of William H. Hirsch Regarding Invalidity of the Venetec Patents Pursuant to Rule 26(a)(2)(B), *Venetec International Inc. v. Nexus Medical, LLC*, U.S. District Court for Delaware. Case No. 07-CV-0057, Jul. 18, 2008, 39 pgs. cited byother.

First Supplemental Complaint [dated Jul. 24, 2007], *Venetec Int'l, Inc. v. Nexus Medical, LLC*, USDC D.Del., Case No. 1:07-CV-00057.

Hi-Tech Products Material Data Sheet entitled "Tricot PSA" (printed prior to Jul. 13, 2006).

Interview Summary in the Ex Parte Reexamination of the '150 patent, U.S. Appl. No. 90/010,211, dated Dec. 19, 2008, 3 pgs.

Interview Summary in the Ex Parte Reexamination of the '979 patent, U.S. Appl. No. 90/010,167, dated Dec. 19, 2008, 4 pgs.

Joint Claim Construction Chart; *Venetec International Inc. v. Nexus Medical, LLC*, U.S. District Court for Delaware, Case No. 07-CV-0057***, Oct. 10, 2008, 91 pgs.

Judge Thynge's Order Denying Nexus Motion to Stay Proceedings Pending Reexamination, *Venetec International Inc. v. Nexus Medical, LLC*, U.S. District Court for Delaware, Case No. 07-CV 0057***, 1 pg. (Oct. 12, 2007).

Memorandum Order; *Venetec International Inc. v. Nexus Medical, LLC*, U.S. District Court for Delaware, Case No. 07-CV-0057***, Mar. 28, 2008, 16 pgs.

Nexus Medical, LLC's First Amended Answer and Counterclaim to Venetec International, Inc.'s Second Supplemental Complaint and Counterclaim; *Venetec International Inc. v. Nexus Medical, LLC*, U.S. District Court for Delaware, Case No. 07-CV-0057, 50pgs. (Mar. 10, 2008).

Nexus Medical LLC's Opening Claim Construction Brief; *Venetec International Inc. v. Nexus Medical, LLC*, U.S. District Court for Delaware, Case No. 07-CV-0057***, Oct. 10, 2008.

Nexus Medical, LLC's Answer to Venetec International, Inc.'s Complaint and Counterclaim [dated Mar. 22, 2007]. *Venetec Int'l, Inc. v. Nexus Medical, LLC*, USDC D.Del., Case No. 1:07-CV-00057.

Nexus Medical, LLC's Answer to Venetec International, Inc.'s First Supplemental Complaint and Counterclaim [dated Aug. 8, 2007]. *Venetec Int'l, Inc. v. Nexus Medical, LLC*, USDC D.Del., Case No. 1:07-CV-00057.

Nexus Medical, LLC's Answer to Venetec International, Inc.'s Second Supplemental Complaint and Counterclaim [filed Sep. 19, 2007]. *Venetec Int'l, Inc. v. Nexus Medical, LLC*, USDC D.Del., Case No. 1:07-CV-00057.

Nexus Medical, LLC's Objections and Responses to Venetec International, Inc's First Set of Interrogatories, *Venetec International Inc. v. Nexus Medical, LLC*, U.S District Court for Delaware Case No. 07-CV-0057***. (Aug. 27, 2007).

Nexus' letter to Judge Thynge dated Sep. 27, 2007, *Venetec International Inc. v. Nexus Medical, LLC*, U.S. District Court for Delaware, Case No. 07-CV-0057***.

Nexus' Opposition to Venetec's Motion for Partial Judgement on the Pleadings, *Venetec International Inc. v. Nexus Medical, LLC*, U.S. District Court for Delaware, Case No. 07-CV-0057, 28 pgs. (Oct. 15, 2007).

Notice of Assignment of Inter Partes Reexamination Request for the '485 patent, *Venetec International Inc. v. Nexus Medical, LLC*, U,S. District Court for Delaware,Case No. 07-CV-0057 1 pg. (dated Jul. 10, 2007).

Notice of Assignment of Reexamination, Application No. 90/010,211, dated Jul. 7, 2008, 1 pg.

Notice of Reexamination Request Filing Date, U.S. Appl. No. 90/010,211, dated Jul. 7, 2008, 1 pg.

Office Action in the Ex Parte Reexamination of the '150 patent, U.S. Appl. No. 90/010,211, dated May 11, 2009.

Office Action in the Ex Parte Reexamination of the '979 patent, U.S. Appl. No. 90/010,167, dated May 8, 2009.

Office Action issued to Venetec in the Ex Parte Reexamination of the '150 patent, U.S. Appl. No. 90/010,211, dated Nov. 7, 2008, 20 pgs.

Office Action issued to Venetec in the Ex Parte Reexamination of the '979 patent, U.S. Appl. No. 90/010,167, dated Nov. 7, 2008, 21 pgs.

Office Action issued to Venetec in the Inter Partes Reexamination, *Venetec International Inc. v. Nexus Medical, LLC*, U.S. District Court for Delaware, Case No. 07-CV-0057***, 23 pgs. (dated Sep. 21, 2007).

Order Granting Inter Partes Reexamination, *Venetec International Inc. v. Nexus Medical, LLC*, U.S. District Court for Delaware, Case No. 07-CV-0057***. Sep. 21, 2007.

Order Granting Request for Ex Parte Reexamination of the '150 patent, U.S. Appl. No. 90/010,211, dated Jul. 29, 2008, 16 pgs.

Order Granting Request for Ex Partes Reexamination, Ex Parte Reexamination of the '979 patent, U.S. Appl. No. 90/010,167, dated Jul. 29, 2008, 14 pgs.

Order Granting Request for Inter Partes Reexamination & Reexamination Non-Final Office Action, Inter Partes Reexamination No. 95/000,271, dated Sep. 21, 2007,50 pgs.

Patent Owner's Response to Office Action issued to Venetec in the Ex Parte Reexamination of the '150 patent, U.S. Appl. No. 90/010,211, dated Jan. 7, 2009, 36 pgs.

Patent Owner's Response to Office Action issued to Venetec in the Ex Parte Reexamination of the '979 patent, U.S. Appl. No. 90/010,167, dated Jan. 7, 2009.

Patent Owner's Response to Office Action, Inter Partes Reexamination No. 95/000,271, dated Nov. 21, 2007, 90 pgs.

Patent Owner's Supplemental Response to Office Action, Inter Partes Reexamination No. 95/000,271, dated Sep. 29, 2008, 46 pgs.

Patent Owner's Supplemental Response to Office Action, Inter Partes Reexamination No. 95/000,271, dated Dec. 21, 2007, 46 pgs.

PCT/US06/34203 filed Aug. 31, 2006 International Search Report dated Aug. 7, 2007.

EP 20747735.7 filed Aug. 18, 2021, Extended European Search Report dated Sep. 6, 2022.

PCT/US2020/015951 filed Jan. 30, 2020, International Search Report and Written Opinion dated May 7, 2020.

U.S. Appl. No. 16/394,969, filed Apr. 25, 2019 Advisory Action dated May 5, 2022.

U.S. Appl. No. 16/394,969, filed Apr. 25, 2019 Non-Final Office Action dated Jun. 14, 2022.

U.S. Appl. No. 16/777,714, filed Jan. 30, 2020 Advisory Action dated Feb. 25, 2022.

U.S. Appl. No. 16/777,714, filed Jan. 30, 2020 Examiner's Answer dated Jul. 26, 2022.

* cited by examiner

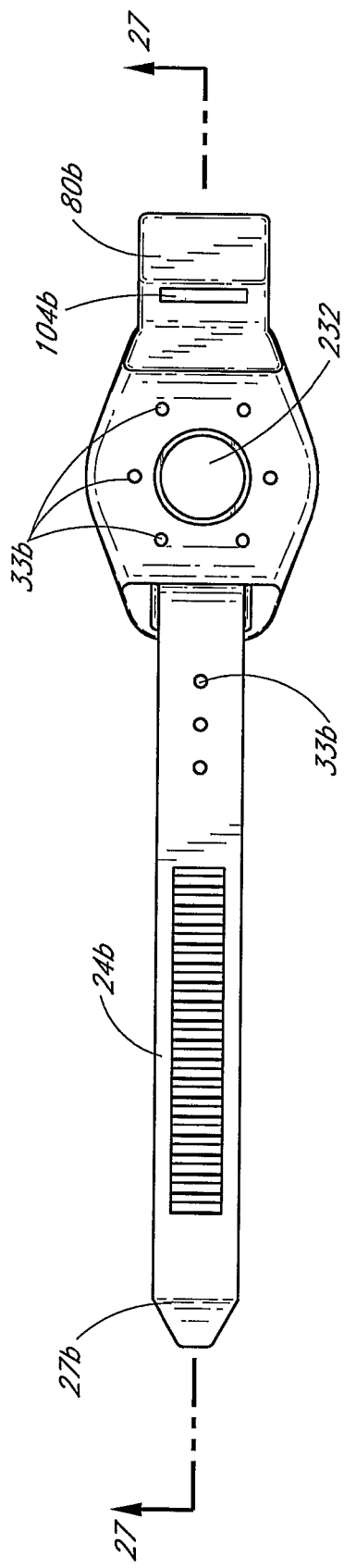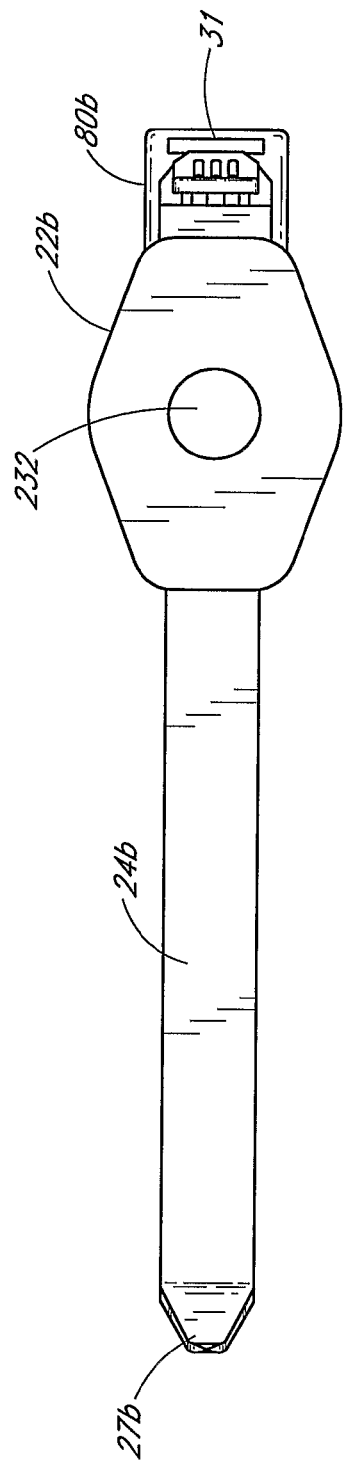
FIG. 23
FIG. 24

ANCHORING SYSTEM FOR A CATHETER

RELATED APPLICATIONS

This application is a continuation of U.S. patent application Ser. No. 15/489,594, filed Apr. 17, 2017, now U.S. Pat. No. 10,561,815, which is a continuation of U.S. patent application Ser. No. 12/063,225, filed Feb. 7, 2008, now U.S. Pat. No. 9,642,987, which is a U.S. national stage of International Patent Application No. PCT/US2006/034203, filed Aug. 31, 2006, which claims the benefit of U.S. Provisional Application No. 60/713,004, filed Aug. 31, 2005, each of which is hereby incorporated by reference in its entirety.

BACKGROUND

1. Field of the Invention

The present invention relates to an anchoring system for securing a medical article to a patient to inhibit movement or migration of the medical article relative to the patient.

2. Description of Related Art

Hospitalized patients often have limited mobility due either to their condition or to doctor's orders. Such patients must lie in bed and not move about their hospital room, even to urinate. As such, a Foley catheter is often used with the bed-confined patient to drain urine from the patient's bladder. Use of a Foley catheter thus eliminates toilet trips as well as reduces bedpan use.

A Foley catheter typically includes two coaxial lumens: a drainage lumen and an inflation lumen. The inflation lumen communicates with an inflation balloon located at the tip of the catheter (i.e., the catheter proximal end). The proximal end of the drainage lumen includes one or more influent openings to receive urine from the bladder. The lumens usually diverge in a Y-type pattern at the distal end of the catheter to form an effluent port and an inflation port.

In use, a healthcare provider inserts the Foley catheter through the urinary tract of the patient to locate the tip of the catheter within the patient's bladder. Although the catheter usually includes a siliconized outer coating as provided by the manufacturer, healthcare providers often apply further lubricant, such as, for example, water-based jelly. The provider then inflates the balloon by attaching the inflation port to a source of pressurized working fluid (e.g., saline solution). Once inflated, a valve, which is located at the inflation port, inhibits the flow of fluid from the inflation lumen and the balloon to keep the balloon inflated. The inflated balloon is intended to prevent the catheter from unintentionally dislodging from the bladder. The healthcare provider then connects the distal end of the drainage lumen (i.e., its effluent port) to a drainage tube leading to a collection container.

The healthcare provider usually secures the distal end of the catheter to the patient using tape. The healthcare provider commonly places long pieces of tape across the distal end of the catheter in a crisscross pattern to secure the catheter distal end to the inner thigh of the patient. This securement is intended to inhibit disconnection between the catheter and the drainage tube, as well as to prevent the catheter or drainage tube from snagging on the bed rail or other objects.

Taped connections, however, often collect contaminants and dirt. Tape also becomes non-adherent to the siliconized surface of the catheter. Normal protocol therefore requires periodic tape changes in order to inhibit germ growth and restore adherence at the securement site. Frequent tape changes though lead to another problem: excoriation of the patient's skin. In addition, valuable time is spent applying and reapplying the tape to secure the catheter. And healthcare providers often remove their gloves when taping because most find the taping procedure difficult and cumbersome when wearing gloves. Not only does this further lengthen the procedure, but it also subjects the healthcare provider to possible infection.

SUMMARY

One aspect of the present invention thus involves an anchoring system for securing a catheter to a body of a patient, the catheter comprising a relatively soft tube for insertion into the patient connected to a relatively rigid connector fitting. The anchoring system comprises an anchor pad having an upper surface and a lower surface, at least a portion of the lower surface having adhesive for contacting a patient's skin. The anchoring system further comprises a retainer rotatably attached to the upper surface of the anchor pad and comprising a base and a strap, the strap being sized to wrap around the catheter distal to a Y-site of the catheter. The retainer has an interengaging structure which secures the strap such that the catheter is secured to the base. The retainer and catheter contact each other over a contact area to provide frictional interaction therebetween. The frictional interaction is sufficient to inhibit longitudinal movement of the catheter relative to the retainer.

Another aspect is an anchoring system for securing a catheter to a body of a patient, the catheter comprising a relatively soft tube for insertion into the patient connected to a relatively rigid connector fitting. The anchoring system comprises an anchor-pad that has an upper surface and a lower surface, at least a portion of the lower surface has an adhesive surface to attach the anchor pad to the body of the patient. The anchoring system further comprises a retainer mounted on the upper surface of the anchor pad. The retainer is capable of receiving a portion of the catheter. The retainer comprises a base and a strap. The base has a contact area. At least a portion of the strap being movable relative to the base so as to move between an open position and a closed position. The strap lies above at least part of the contact area when in the closed position and is sized to wrap around the catheter distal to a Y-site of the catheter. The anchoring system further comprises a latch mechanism configured to secure the strap when in the closed position such that the catheter is secured to the base. The retainer and catheter contacting each other over at least a portion of the contact area to provide frictional interaction therebetween. The frictional interaction being sufficient to inhibit longitudinal movement of the catheter relative to the retainer.

Another aspect is a method for releasably anchoring a catheter including a relatively soft tube for insertion into the patient connected to a relatively rigid connector fitting. The method comprises providing an anchoring device having an adhesive lower surface, and a retainer comprising a base and a strap, inserting a distal portion of the medical article into a contact area of the retainer such that at least a portion of the connector fitting lies over the base, and positioning the strap over at least a portion of the medical article. The method further comprises securing the strap such that the retainer and medical article contact each other over the contact area to provide frictional interaction therebetween, the frictional interaction being sufficient to inhibit longitudinal movement of the medical article relative to the retainer and securing the anchoring device to the skin of the patient via the adhesive lower surface of the anchoring device.

Further aspects, features and advantages of the present invention will become apparent from the detailed description of the preferred embodiments that follows.

BRIEF DESCRIPTION OF THE DRAWINGS

The above mentioned and other features of the invention will now be described with reference to the drawings of embodiments of the present anchoring system. The illustrated embodiments of the anchoring system are intended to illustrate, but not to limit the invention. The drawings contain the following figures:

FIG. 23 is a top view of the retainer from FIG. 22 showing a plurality of barbs on a portion of the inner surface of the channel.

FIG. 24 is a bottom view of the retainer from FIG. 22 showing a through-hole in the base of the retainer.

DETAILED DESCRIPTION OF THE PREFERRED EMBODIMENTS

Figure 1:
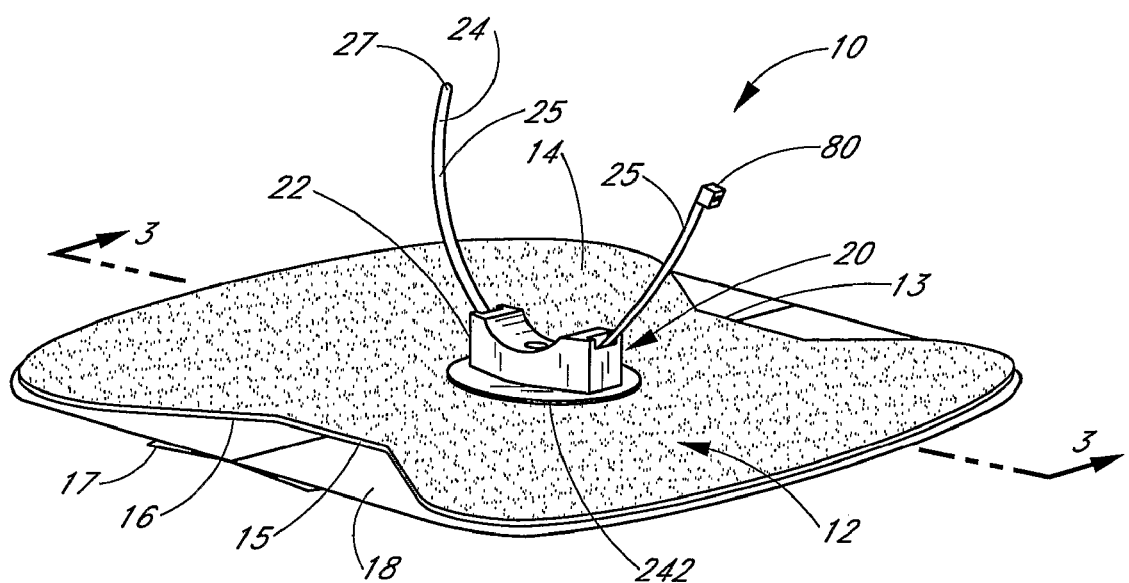
FIG. 1 is a perspective view of an anchoring system in accordance with an embodiment of the present invention.

The present embodiments of the medical article anchoring system are disclosed in the context of an exemplary Foley type catheter. The principles of the present invention, however, are not limited to Foley catheters. Instead, it will be understood by one of skill in this art, in light of the present disclosure, that the anchoring system and retainer disclosed herein also can be successfully utilized in connection with other types of medical articles, including other types of catheters, fluid drainage and delivery tubes and electrical wires. For example, but without limitation, the retainer disclosed herein can also be configured to receive and secure central venous catheters, peripherally inserted central catheters, hemodialysis catheters, surgical drainage tubes, feeding tubes, chest tubes, nasogastric tubes, scopes, as well as electrical wires or cables connected to external or implanted electronic devices or sensors. One skilled in the art can also find additional applications for the devices and systems disclosed herein. Thus, the illustration and descriptions of the anchoring system in connection with a Foley catheter are merely exemplary applications of the anchoring system.

The anchoring system described herein is especially adapted to arrest axial movement of a catheter with a slippery coating, as well as hold the catheter against the patient. For this purpose, the anchoring system 10 utilizes one or more retention mechanisms. The anchoring system accomplishes this though without meaningfully impairing (i.e., substantially occluding) the fluid flow through the catheter to a degree that would create complications for a patient. As described below, such retention mechanisms involve, among others, the shape of the channel that retains a section of the catheter, retaining structure either aligned with or positioned within the channel, and/or a securement barb(s) and/or friction ridge(s) that bites into the catheter body without substantially occluding the catheter drainage lumen.

In certain embodiments, the anchoring system releasably engages the catheter. This allows the catheter to be disconnected from the anchoring system, and from the patient, for any of a variety of known purposes. For instance, the healthcare provider may want to remove the catheter from the anchoring system to ease disconnection of the catheter from the drainage tube or to clean the patient. In such embodiments, the disengagement of the catheter from the anchoring system, however, can be accomplished without removing the anchoring system from the patient. An exemplary releasable strap that may be utilized with the anchoring system is described in U.S. Pat. No. 4,236,280, which is hereby incorporated by reference. Alternatively, a strap or other securing means is cut to thereby release the catheter from the retainer. In certain embodiments that have a strap that is not integral to the base, the strap may be cut and replaced with an uncut strap. The cut strap is removed from the conduit passing through the base. The uncut strap is then inserted through the same conduit. The retainer is thereby ready for re-engaging with the same or different catheter.

Before describing the present anchoring system in detail, a brief description of a Foley catheter is provided to assist the reader's understanding of the exemplary embodiment that follows. As best understood from FIG. 6, the catheter 8 includes a proximal tip with an inflatable balloon (not shown) and a distal end 110. The distal end 110 includes a Y-site 112 formed by an inflation branch 114 and a drainage branch 116. The drainage branch 116 and the inflation branch 114 merge together at the Y-site 112. The lumens of these branches assume either a coaxial or side-by-side arrangement on the proximal side of the Y-site 112 to form a main catheter body 118. On the distal side of the Y-site 112, a webbing 120 extends between the two branches 114, 116 at a point next to the Y-site 112. The drainage branch 116 receives a connector fitting 82. Preferably, the connector fitting 82 is semi-rigid and fits within a portion of the drainage branch 118 distal of the Y-site 112. The region of the drainage branch 118 which receives the semi-rigid connector fitting 82 is preferably the portion of the catheter 8 that is retained by the retainer. The connector fitting 82 allows the retainer to compress the drainage branch 116 without significantly occluding the lumen within the drainage branch 116.

Figure 2:
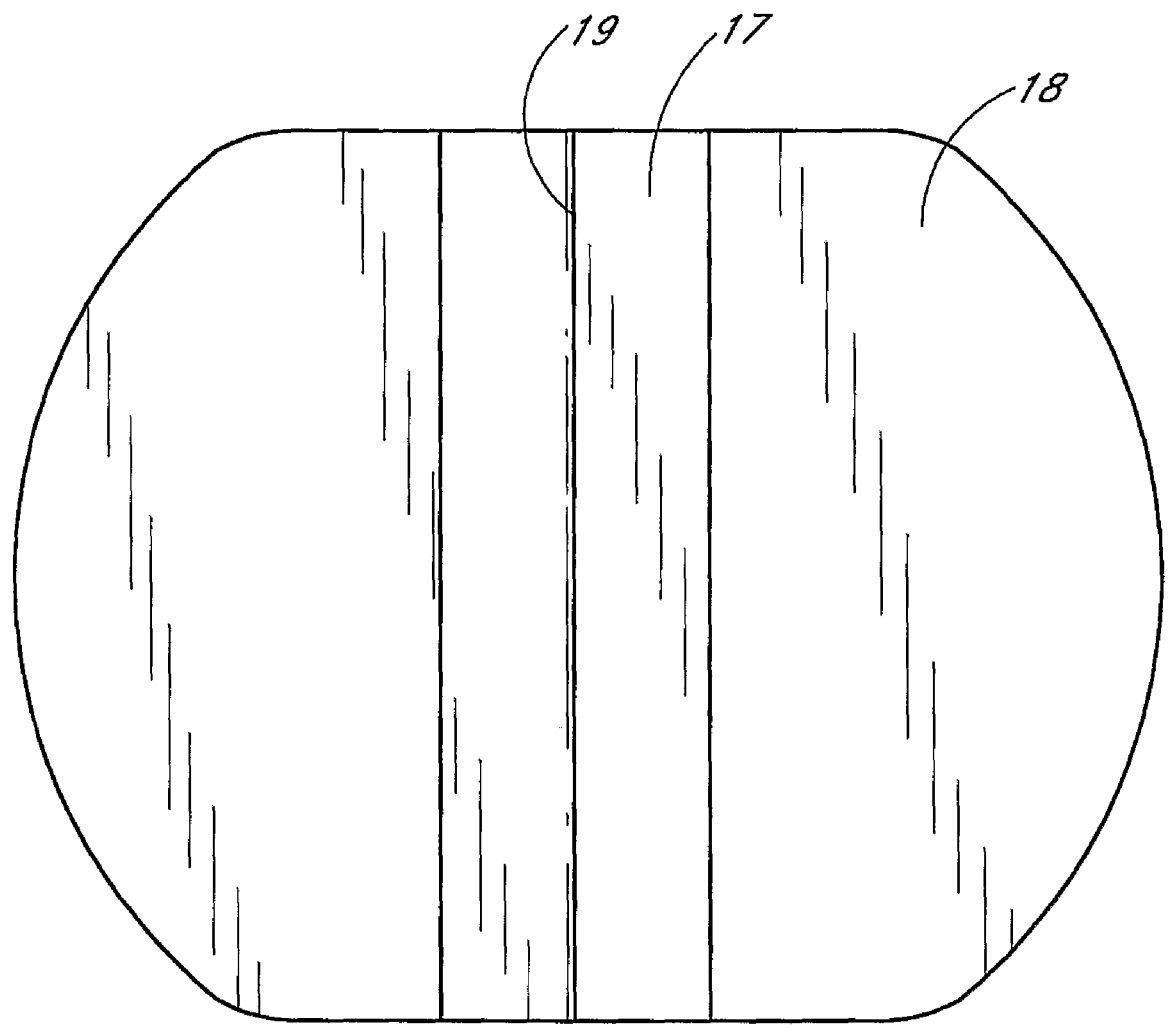
FIG. 2 is a bottom view of the anchoring system of FIG. 1.

With reference now to FIGS. 1 and 2, the anchoring system 10 includes an anchor pad 12 and a retainer 20. The anchor pad 12 secures the retainer 20 to a patient's skin. The anchor pad 12 has a lower adhesive surface 16 which adheres to the skin of a patient and a roughened upper surface 14 which supports the retainer 20. The retainer 20 is configured to accept and retain a section of a Foley catheter 8 or other medical article within the anchoring system 10. In the illustrated embodiment, the retainer 20 comprises a base 22 and a strap 24. The strap 24 may be detachably or permanently secured to the base 22 and moveable between open and closed positions.

To assist in the description of these components of the anchoring system 10, the following coordinate terms are used. A "longitudinal axis" is generally parallel to the section of the catheter 8 retained by the anchoring system 10. A "lateral axis" is normal to the longitudinal axis and is generally parallel to the plane of the anchor pad 12. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. Also, the terms "proximal" and "distal", which are used to describe the present anchoring system 10, are used consistently with the description of the exemplary application. Thus, proximal and distal are used in reference to the center of the patient's body. A detailed description of the anchoring system 10, and its associated method of use, now follows.

FIGS. 1 and 2 illustrate an anchor pad 12 which desirably comprises a laminate structure with an upper foam or woven material (e.g. tricot) layer (e.g., closed-cell polyethylene foam), and a lower adhesive layer. The lower adhesive layer constitutes the lower surface 16 of the anchor pad 12. The lower surface 16 desirably is a medical-grade adhesive and can be either diaphoretic or non-diaphoretic, depending upon the particular application. Such foam or woven material with an adhesive layer is available commercially from Avery Dennison of Painsville, Ohio. Although not illustrated, it will be understood that the anchor pad 12 can include suture holes in addition to the adhesive layer to further secure the anchor pad 12 to the patient's skin.

A surface of the upper foam layer constitutes an upper surface 14 of the anchor pad 12. The upper surface 14 can be roughened by corona-treating the foam or woven material with a low electric charge. The roughened or porous upper surface 14 can improve the quality of the adhesive joint (which is described below) between the base 22 and the anchor pad 12. In the alternative, the flexible anchor pad 12 can comprise a medical-grade adhesive lower layer, an inner foam layer and an upper paper or other woven or nonwoven cloth layer.

A removable paper or plastic release liner 18 desirably covers the adhesive lower surface 16 before use. The liner 18 preferably resists tearing and desirably is divided into a plurality of pieces to ease attachment of the pad 12 to a patient's skin. In the illustrated embodiment, the liner 18 is split along a center line 19 of the flexible anchor pad 12 in order to expose only half of the adhesive lower surface 16 at one time.

The liner 18 length, as measured in the lateral direction, extends beyond the center line 19 of the anchor pad 12 and is folded over, or back onto the liner 18. This folded over portion defines a pull tab 17 to facilitate removal of the liner 18 from the adhesive lower surface 16. A healthcare provider uses the pull tab 17 by grasping and pulling on it so that the liner 18 is separated from the lower surface 16. The pull tab 17 overcomes any requirement that the healthcare provider pick at a corner, edge or other segment of the liner 18 in order to separate the liner 18 from the adhesive layer. The pull tab 17 of course can be designed in a variety of configurations. For example, the pull tab 17 need not be located along a center line 19 of the anchor pad 12. Rather, the pull tab 17 can be located along any line of the anchor pad 12 in order to ease the application of the anchor pad 12 onto the patient's skin at a specific site. For example, an area of a patient's skin with an abrupt bend, such as at a joint, can require that the pull tab 17 be aligned toward one of the lateral ends of the anchor pad 12 rather than along the center line 19.

In the illustrated embodiment, the anchor pad 12 also desirably includes a pair of opposing concave sections 13, 15 that narrows the center of the anchor pad 12 proximate to the base 22. As a result, the lateral sides of the anchor pad 12 have more contact area which provides greater stability and adhesion to a patient's skin.

The retainer 20 is principally formed by the base 22 and the strap 24. The illustrated strap 24 is a one-piece flexible plastic strap. The strap 24 comprises an elongated base portion 25 having a free end 27. The retainer 20 further comprises interengaging structure to couple the free end 27 to the retainer 20. In the embodiment illustrated in FIG. 3, the interengaging structure comprises a latch mechanism 80 and a plurality of teeth members or protuberances 88. The latch mechanism 80 is integrally formed at the end opposite from the free end 27. The healthcare provider introduces the free end 27 of the base portion 25 into an opening 104 in the latch mechanism 80 so that the plurality of teeth members 88 on the strap 24 with engage with the latch mechanism 80 to lock the strap in a selected position. The free end 27 of the base portion 25 may be tapered toward its extremity, which is rounded, so as to facilitate entry into opening 104 in the latch mechanism 80. The plurality of teeth members or protuberances 88 are provided on the base portion 25 near the free end 27 and facilitate gripping of the free end 27 by the healthcare provider and locking the free end 27 in the latch mechanism 80. The latch mechanism 80 has one or more transversely extending tooth or pawl 90 on the same side as the gripping teeth 88 on the free end 27. The pawl 90 is adapted to cooperate with the teeth members 88 on the base portion 25 so as to retain the base portion 25 within the latch mechanism 80.

Figure 3:
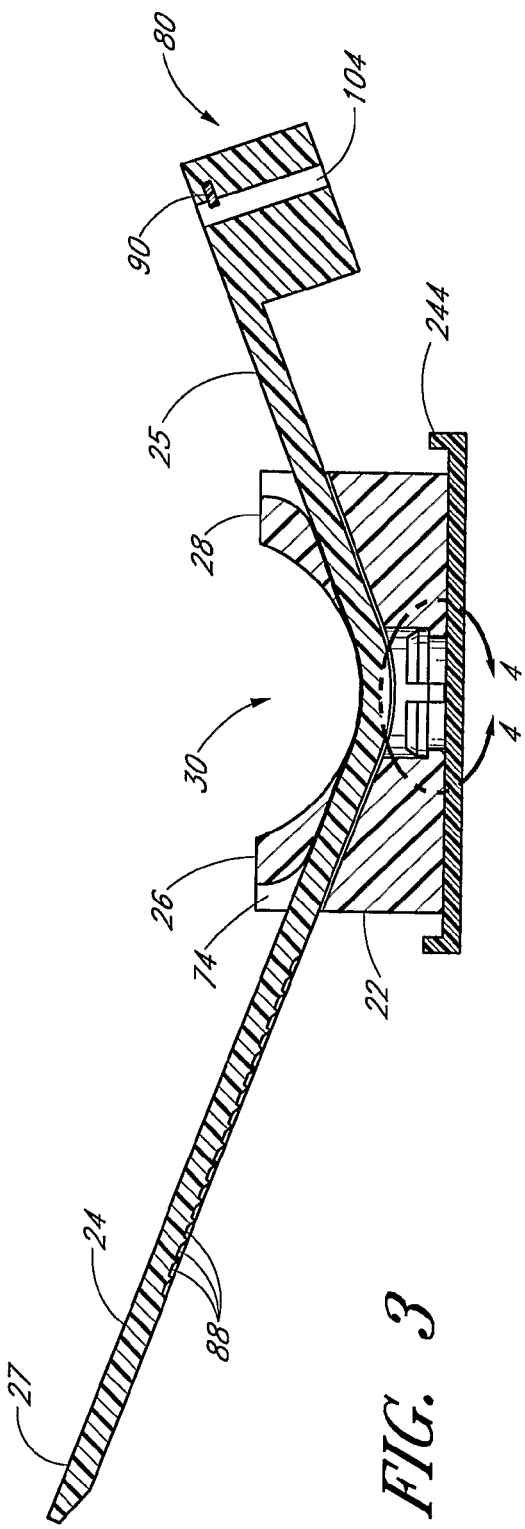
FIG. 3 is a cross-sectional view of the retainer, taken along the line 3-3 of FIG. 1.

As most clearly shown in FIG. 3, a conduit 74 extends through the base 22 and is configured to receive the strap 24. Once inserted into the conduit 74, the strap 24 extends from both ends of the conduit 74. In certain embodiments, the conduit 74 has a width that is less than the width of the base 22. The conduit 74 may have multiple portions aligned in the lateral direction and forming a single path for the strap 24. An opening or window extending through the upper wall of the conduit 74 may separate the conduit portions. The opening or window may advantageously ease insertion of the strap through the conduit 74. The portion of the strap 24 that is exposed through the window forms a portion of the bottom surface of the channel 60.

The conduit may taper in width along at least a portion of its length. For example, the tapering or wide-mouth shapes of the conduit 74 openings eliminate an edge or surface over which the strap 24 could bind. The openings may further curve parallel with the strap 24 when the strap 24 is in the closed position so as to smoothly guide the strap 24 as the strap 24 exits the conduit 74 and wraps around the catheter.

Tapering the ends of the conduit 74 advantageously eases insertion of the strap into the conduit while maintaining a close fit between the walls of the conduit 74 and the strap 24 between the tapering ends. Alternatively, the cross-section of the conduit 74 may substantially exceed the cross-section of the strap 24. Once inserted, the strap 24 is fed through the conduit 74 until the inserted end extends from the base 22.

In the illustrated embodiment, the base 22 and strap 24 are separately formed and assembled to comprise the retainer 20. The retainer 20 is assembled by feeding the strap 24 through the conduit 74. Alternatively, the base 22 and strap 24 can be formed together as a unitary retainer 20. This can be accomplished in any of a variety of ways well known to those skilled in the art. For instance, the entire retainer 20 can be injection molded in order to reduce fabrication costs. Exemplary embodiments of a unitary retainer are described below with reference to FIGS. 9 through 28.

In order to illustrate more clearly the design features of the retainer 20 in FIGS. 1 through 8, the anchor pad 12 of the anchoring system 10 is not shown in FIGS. 3, 4, 6, 7, and 8. In accordance with the preferred embodiment, however, the entire anchoring system 10 is assembled in accordance with the above-description (e.g., the anchor pad 12 is attached to the retainer 20) and is sterilized before use.

As will be apparent from the below description, several features of the retainer (e.g., the strap) desirably are flexible. Suitable ridged but flexible materials include, for example, but without limitation, plastics, polymers or composites such as polypropylene, polyethylene, polycarbonate, polyvinylchloride, acrylonitrile butadiene styrene, nylon, olefin, acrylic, polyester, as well as moldable silicon, thermoplastic urethane, thermoplastic elastomers, thermoset plastics and the like. The illustrated base 22 may be formed by injection molded using polyethylene or polypropylene material or nylon. However, other materials can be utilized, and the retainer 20 can comprise a unitary base 22 and strap 24.

With reference to FIG. 3, the base 22 in the illustrated embodiment comprises an elongated body of a generally parallelepiped shape. The base 22, however, can be configured in a wide variety of shapes as well, such as circular, square, triangular or the like in order to suit a particular application. The width of the strap 24 desirably is sufficiently long to provide stability to the catheter along its length. That is, the width of the retained catheter portion is sufficient to inhibit rocking of the catheter relative to the retainer 20 (i.e., to prevent the retainer 20 from acting as a fulcrum for the catheter). Also, the lateral dimension of the base 22 desirably allows the healthcare provider to easily and naturally grip the base 22.

The base 22 includes first and second sides 26, 28. The first side 26 lies generally at one lateral end of the base 22, and the second side 28 lies at an opposite lateral end of the base 22.

Figure 6:
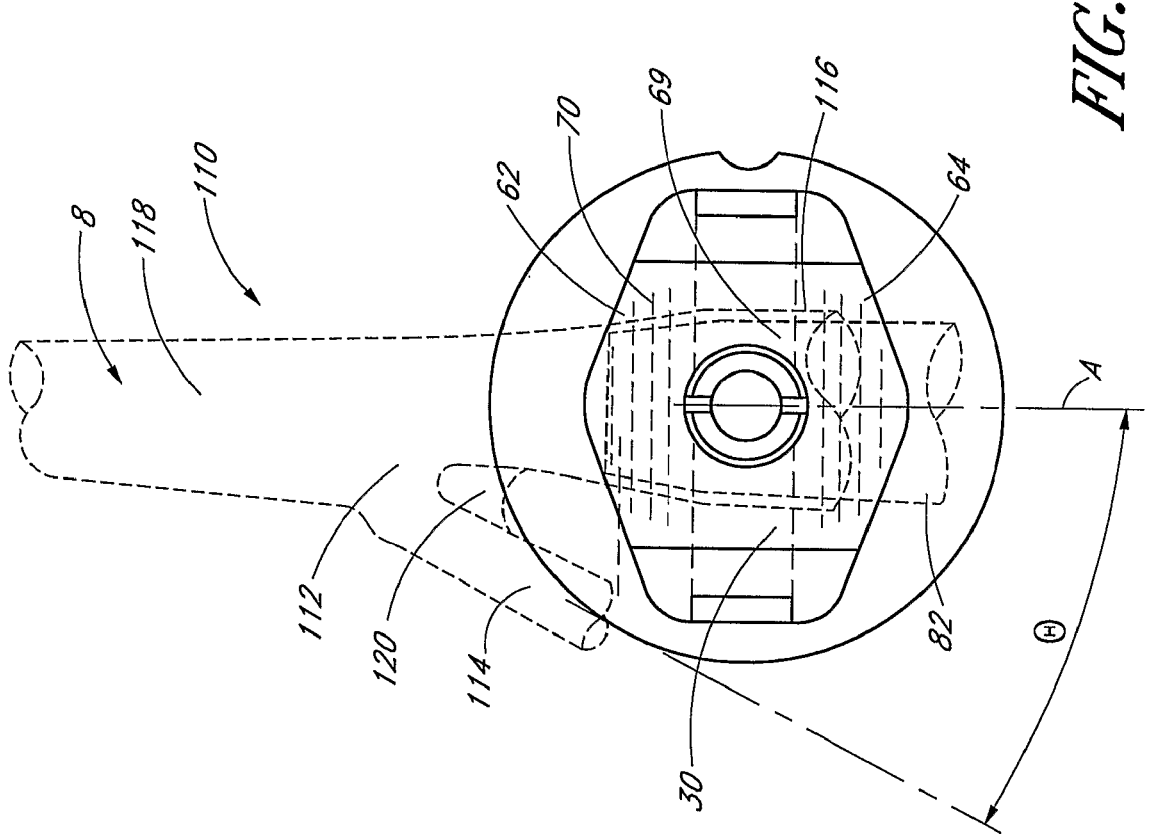
FIG. 6 is a top plan view of the retainer of FIG. 1 with the strap removed from the retainer and a catheter aligned above the anchoring system.

A groove 30 or concave surface is formed on the base 22 between the first side 26 and the second side 28. In the illustrated embodiment, the groove 30 has generally a truncated generally circular cross-sectional shape. As best seen in FIG. 6, the groove 30 is consistent in width along the longitudinal axis. In certain embodiments, the groove 30 varies in width (i.e., in the lateral direction) along the longitudinal axis. That is, in certain embodiments, the side walls of the groove 30 diverge from each other in, for example, a generally linear manner from one longitudinal side of the retainer 20 to the other longitudinal side of the retainer.

The base 22 of the retainer 20 engages with the anchor pad 12. In the illustrated embodiment, the retainer 20 is rotatably mounted onto the anchor pad 12. The retainer 20 may be rotated by at least some degree, and preferably by 360°, relative to the anchor pad 12, as described below. For this purpose and as most clearly shown in FIG. 5, a mounting post 226 is attached to the anchor pad 12 and a hole 232 is formed in the base 22 of the retainer 20.

Figure 4:
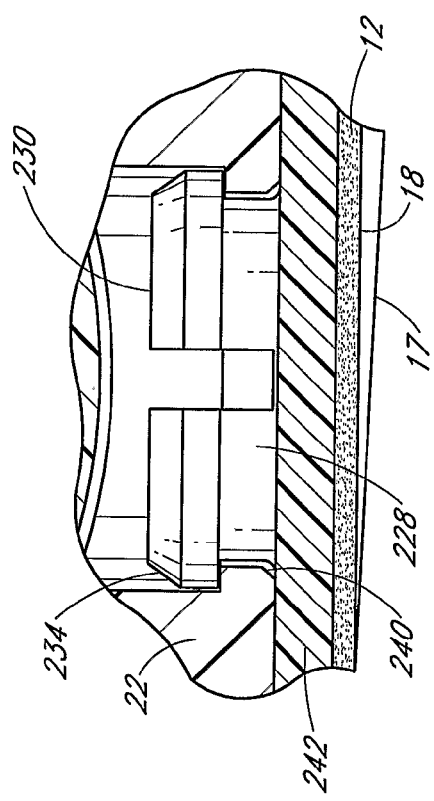
FIG. 4 is an enlarged detail view of a cross-sectional view of a rotatable mount of FIG. 3 circumscribed by line 4-4.
Figure 5:
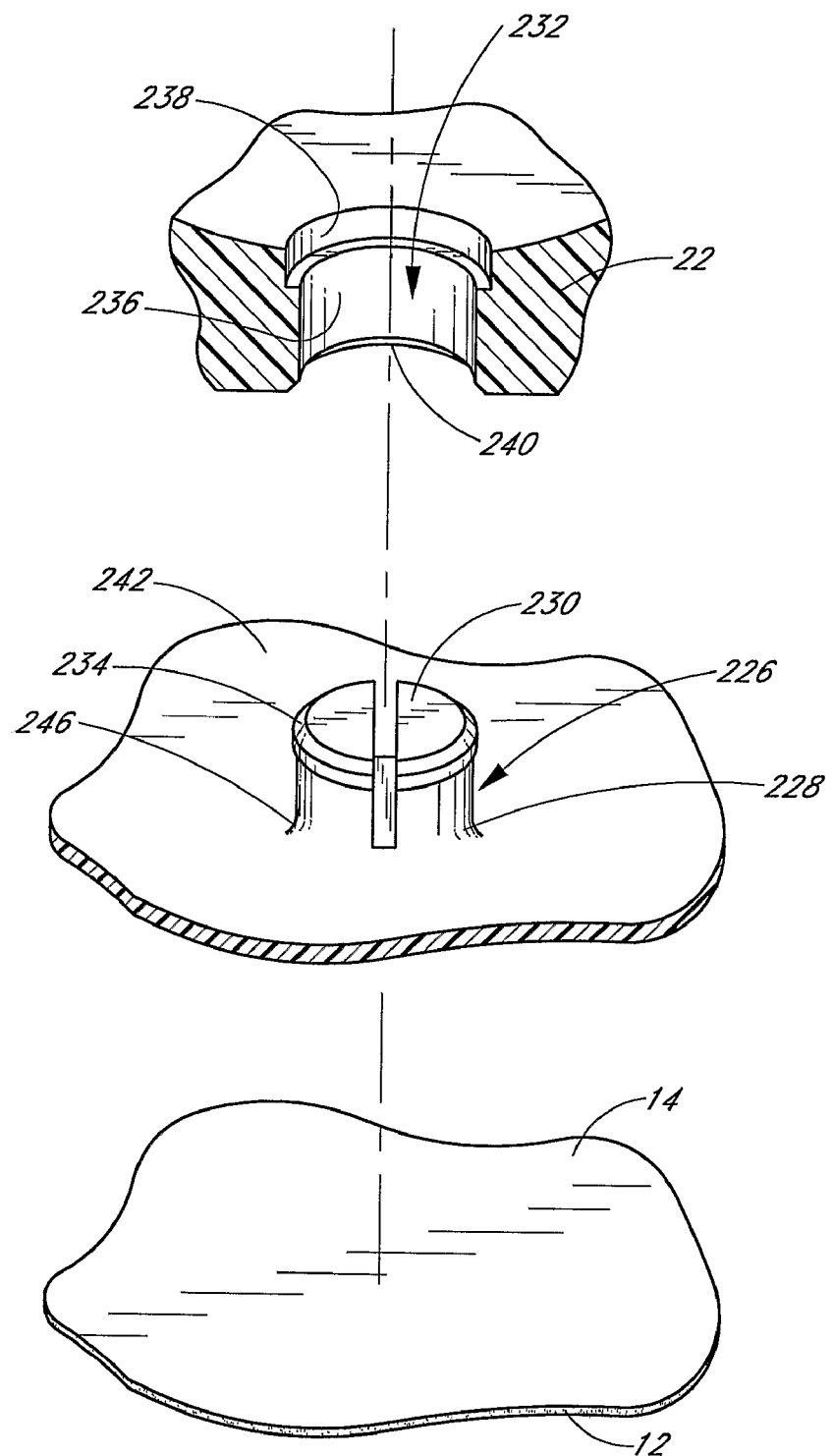
FIG. 5 is an enlarged, exploded detail view of the rotatable mount and a through-hole in the retainer of FIG. 3.

As best seen in FIGS. 3 through 5, the mounting post 226 is attached to the anchor pad 12. The through-hole 232 is formed in the base 22 of the retainer 20. The mounting post 226 and through-hole 232 allow the retainer 20 to pivot relative to the anchor pad 12. In the illustrated embodiment, the retainer 20 can be rotated 360° relative to a central pivot point fixed to the anchor pad 12; however, the degree of rotation also can be confined.

Relative rotation is advantageous to assist the medical provider in attaching and detaching the retainer 20 to the catheter (not shown). Relative rotation is also advantageous to assist the healthcare provider in adjusting the attached catheter or retainer assemblage so that the catheter is less likely to become kinked or snagged on an object. Relative rotation is further advantageous to assist in positioning the catheter in-line with the drainage lumen or other object. In addition, the healthcare provider need not precisely align the retainer relative to an axis of the catheter before attaching the pad to the patient's skin. The healthcare provider can coarsely align the anchoring system on the patient, adhere the pad 12 to the patient's skin and then allow the retainer 20 to rotate so as to align the groove 30 of the base 22 with the longitudinal axis of the catheter. The rotatable nature of the retainer 20 thus eases connection and disconnection of the catheter with the retainer 20. The rotatable nature also permits the patient to move without kinking the catheter.

As best seen in FIGS. 4 and 5, the illustrated mounting post 226 comprises a pedestal 228 and a cap 230 configured for acceptance into a through-hole 232 formed in the base 22 of the retainer 20. The pedestal 228 is attached to and extends upwardly from a mounting base 242. The pedestal 228 can have a variety of transverse heights depending upon the particular application and the particular retainer to which it interacts. For anchoring Foley catheters and for use with the retainer described in FIG. 1, the pedestal 228 desirably has a transverse height slightly smaller than that of the base 22 at the location of the hole 232; that is, the height can be about 1-5 mm, and more particularly about 3 mm; however, other heights are also possible. The illustrated pedestal 228 has a generally cylindrical shape, but can be configured in a variety of other shapes, which can match the shape of the hole 232 in the retainer base 22. The diameter of the pedestal 228 is sufficient to perform its structural function of coupling the anchor pad 12 to the base 22 without significantly bending or breaking and desirably has a diameter of about 1 to 8 mm and more particularly a diameter of about 6 mm; however, larger or smaller diameters are also possible. Thus, the diameter of the pedestal 228 is desirably about twice the height of the pedestal 228. The pedestal 228 is flared at the bottom to form an annular fillet 246. The fillet 246 provides structural strength to the pedestal 228 to resist shear and other forces that can otherwise cause the pedestal to break off from the mounting base 242 or otherwise fail.

The cap 230 extends radially outward from the top portion of the pedestal 228. The cap 230 assists in coupling the mounting base 242 to the base 22 by inhibiting separation of the pedestal 228 from the base 22, as explained below. The radial width of the cap 230 can vary, depending upon the particular application, and desirably is about 1-5 mm, and more particularly about 2 mm; however, larger or smaller widths are also possible. The illustrated cap 230 has a cross sectional shape generally similar to that of the pedestal 228 for ease of manufacture, however, it can be configured in a variety of other cross sectional shapes to generally match the shape of the through-hole 232 in the base 22, which is described below. The cap 230 desirably extends beyond the circumference of the pedestal 228 to assist in securely coupling the mounting base 242 to the base 22. However, the cap 230 need not circumscribe the entire pedestal 228 and can comprise only a single radial member that extends outwardly from the pedestal 228. The transverse thickness of the cap 230 is sufficient to perform its structural function of coupling the mounting base 242 to the base 22 without significantly bending or breaking and desirably has a thickness of about 0.5 to 2 mm and more particularly a thickness of about 1 mm; however, larger or smaller thicknesses are also possible. A chamfer 234 can be formed on an upper peripheral edge of the cap 230 to assist in the assembly of the mounting post 226, as described below. The illustrated chamfer 234 transversely extends for about one-half the thickness of the cap 230. In an embodiment, the mounting post 226 further includes a slot extending axially through at least a portion of the mounting post 226. The slot facilitates coupling between the mounting post 226/mounting base 242 and the retainer via the through-hole 232 by allowing portions of the cap 230 to flex radially inwards as the cap 230 is urged through the through-hole 232 during assembly, as described below.

The mounting post pedestal 228 desirably has a smooth side surfaces to facilitate sliding of the base 22 relative to the mounting post 226, such that the mounting post 226 provide a bearing surface for the retainer base 22. The top of the cap 230 additionally is smooth and planar to present a surface that is generally flush with the surface of the base 22 within the channel. It is understood, however, that the configuration of the channel surface of the base 22, results in an imperfectly flush surface between the base and the cap 230, although the top of the cap 230 could be configured to match the configuration of the surface of the base 22 and thereby present a perfectly flush surface. The mounting post 226 has a two-piece configuration for ease of manufacture and strength; however, the mounting post 226 can alternatively comprise a single component. Although the illustrated mounting post 226 is generally mushroom shaped with a generally flat top, the mounting post 226 can also be generally T-shaped, inversely L-shaped and the like.

The mounting post 226 is desirably formed in unity with the mounting base 242 for structural strength. However, the mounting post 226 and the mounting base 242 can comprise separate components, as noted below. The mounting base 242 provides a larger footprint, relative to that of the mounting post 226, such that in an embodiment at least a portion of the perimeter of the mounting post 226/mounting base 242 structure extends horizontally beyond a perimeter of the retainer base 22, so that the mounting post 226 can be more securely attached to the anchor pad 12 and inhibit unintended separation of the mounting post 226 from the anchor pad 12. For example, if the anchoring system 10 is adhered to the inner thigh of a bedridden patient, movement of the patient can generate forces on the anchoring system 10. Thus, the larger footprint which the mounting base 242 provides, and which the mounting post 226 is preferably in unity with, provides increased securement between the mounting post 226 and anchor pad 12 and enhances the robustness of the anchoring system.

The mounting base 242 is generally planar to match the upper surface 14 of the anchor pad 12. The illustrated mounting base 242 also has a circular configuration, with the mounting post 226 located at the center of the base 242 so that the retainer 20 can centrally rotate on the mounting base 242. However, the base can have other shapes as well.

Additionally and as most clearly shown in FIG. 3, an upturned lip 244 may circumscribes the perimeter of the mounting base 242 to form a barrier that inhibits inwardly directed radial forces from shearing or otherwise separating the retainer 20 or mounting post 226 from the mounting base 242. The lip 244 may have a transverse height of about 1-5 mm for this purpose. The lip diameter is slightly larger than the lateral width of the retainer 20 (i.e., larger by about 1 mm); however, the lip 244 can alternatively be arranged to radially abut the retainer 20 when the retainer 20 rotates on the mounting base 242, or to provide a radial clearance between the retainer 20 and the lip 244. The lip 244 additionally does not extend above the bottom of the groove 30 and thus do not present an edge about which the catheter could kink. The lip 244 may be shorter than the mounting post 226. The lip 244 also does not interfere with the free rotation of the retainer 20. However, the mounting base 242 and the retainer 20 can include cooperating structure which establishes incremental angular positions of the retainer 20 as it rotates over the mounting base 242. This can be done by providing a plurality of ratchet teeth about the inner side surface of the lip 244 and a cooperating tang formed on the retainer 20. In this manner, the orientation of the retainer 20 on the mounting base 242 can be set until a sufficient force is applied to the retainer to overcome the engagement between the tang and the corresponding ratchet teeth.

In the illustrated embodiment, as best understood from FIGS. 4 and 5, the base 22 of the retainer 20 has a through-hole 232 sized and configured to receive the post and more preferably to generally match that of the mounting post 226 so that the retainer 20 can rotate relative to the anchor pad 12 about the mounting post 226. The illustrated through-hole 232 extends through the base 22 and has a first or lower diameter 236 and a second or upper diameter 238. The lower diameter 236 is slightly larger than that of the pedestal 228 and the upper diameter 238 is slightly larger than that of the cap 230. The tolerance between the through-hole 232 and the mounting post 226 desirably is about 0.1-0.5 mm and more particularly about 0.1-0.2 mm. Like the mounting post 226, the through-hole 232 has a smooth surface to minimize function when the retainer is rotated. A chamfer 240 can circumscribe the lower portion of the lower diameter 236 to assist in the assembly of the rotatable mounting post 226, as described below.

When assembled, the mounting post 226 is arranged within the through-hole 232 and secured to the anchor pad 12. In particular, the top of the cap 230 is generally flush with the top of the base 22, the cap 230 is housed within the upper diameter 238, the pedestal 228 is housed within the lower diameter 236, and the bottom of the pedestal 228 is secured relative to the anchor pad 12. The mounting base 242 is desirably secured to the upper surface 14 of the anchor pad 12 by a solvent bond adhesive, such as cyanoacrylate or other bonding material. One such adhesive is available commercially as Part No. 4693 from the Minnesota Mining and Manufacturing Company (3M).

One suitable assembly process, advantageously used when the mounting post 226 and mounting base 242 are formed in unity, involves bonding the bottom of the mounting base 242 to the upper surface 14 of the anchor pad 12 and then urging the cap 230 of the mounting post 226 through the through-hole 232. The chamfer 240 that circumscribes the through-hole 232 and the chamfer 234 that circumscribes the cap 230 cooperate to allow the cap 230 to deform and advance through the through-hole 232. Another suitable assembly process, advantageously used when the mounting post 226 and mounting base 242 comprise separate components, involves placing the pedestal 228 through the through-hole 232 such that the pedestal 228 extends through the first diameter 236 while the cap 230 catches on the second diameter 238, then bonding the bottom of the pedestal 228 to the mounting base 242, and then bonding the mounting base 242 to the anchor pad 12. By this configuration, the retainer 20 can rotate 360° relative to the anchor pad 12.

Alternatively, the base 22 is secured to the upper surface 14 by a solvent bond adhesive, such as cyanoacrylate or other bonding material. One such adhesive is available commercially as Part No. 4693 from the Minnesota Mining and Manufacturing Company (3M). In such an embodiment, the retainer 20 is fixedly attached and does not rotate relative to the anchor pad 12.

As also seen in FIG. 3, the strap 24 has an elongate shape which desirably has a sufficient length to circumscribe the retained portion of the catheter. Each end of the strap 24 need not be the same size or shape. In certain embodiments, the strap 24 has a sufficient longitudinal length to cover the groove 30 in the base and to accommodate a portion of the latch mechanism 80. The latch mechanism 80 may be located on an end of the strap 24 or on the base 22. The latch mechanism 80 operates to secure at least an end of the strap 24. The strap 24 also desirably is of a dimension which provides for easy manipulation. For example, the strap's size easily accommodates the grasp of a healthcare provider.

Figure 8:
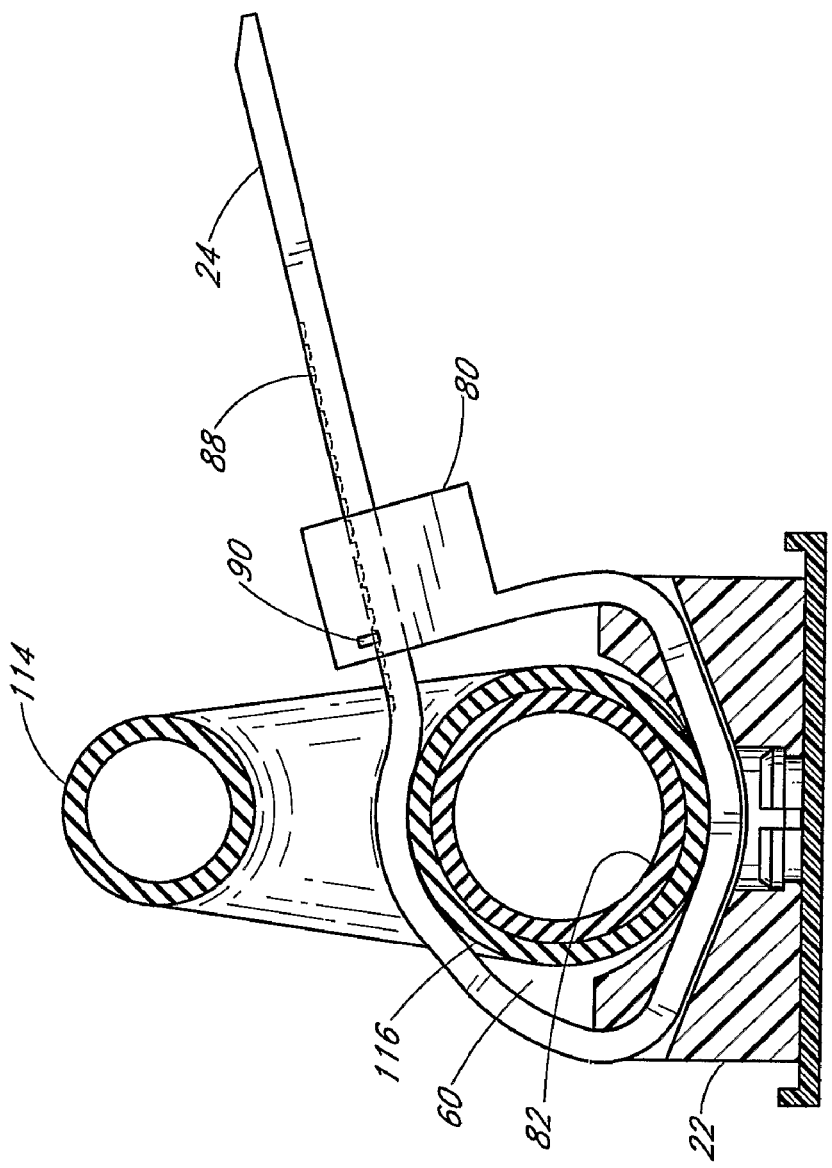
FIG. 8 is a cross-sectional view of the anchoring system of FIG. 1, and illustrates the strap in a closed position with the catheter secured within the channel of the anchoring system.

As most clearly shown in FIG. 8, when the strap 24 is in a closed position an upper groove is formed on an inner side of the strap 24 between the first and second sides 26, 28 of the base 22. The upper groove corresponds generally to the lower groove 30 formed in the base 22. In the illustrated embodiment, the strap 24 mechanically connects to the base 22 while permitting the strap to slide in a lateral direction through the conduit 74 in the base 22. In the illustrated embodiment, the strap 24 is formed of flexible material, desirably of the same material from which the base 22 is comprised.

Figure 7:
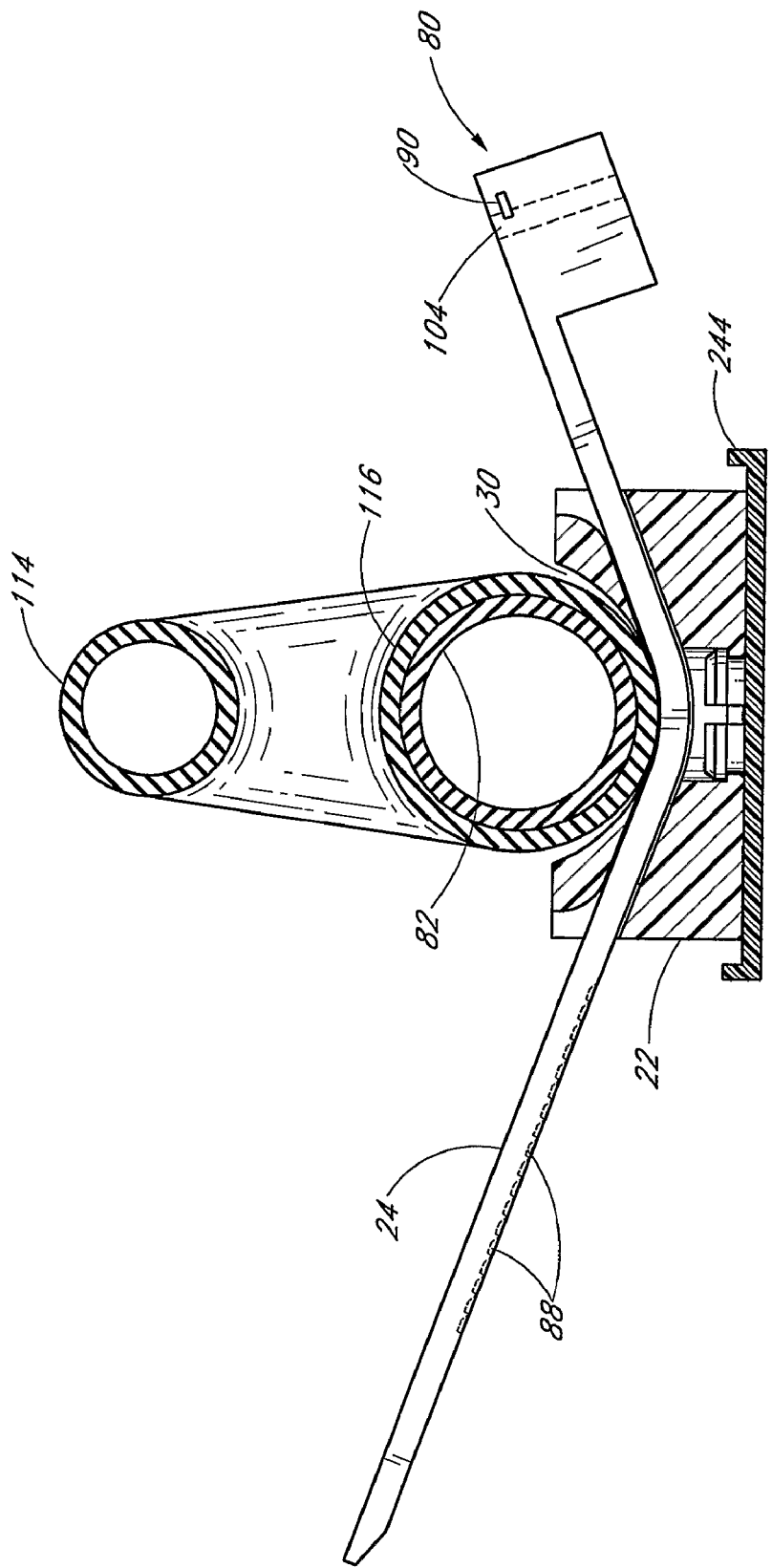
FIG. 7 is a cross-sectional view of the anchoring system of FIG. 1, and illustrates the strap in an open position and a catheter aligned above the anchoring system for insertion therein.

With the strap 24 in the open position, as illustrated in FIG. 7, the groove 30 in the base 22 is exposed. When in the open position, the retainer 20 is capable of receiving a portion (e.g., the drainage branch 116) of the Foley catheter. As most clearly illustrated in FIG. 6, the drainage branch 116 receives a portion of the connector fitting 82. The connector fitting 82 fits within a portion of the drainage branch 118 distal of the Y-site 112. The region of the drainage branch 118 which receives the semi-rigid connector fitting 82 is preferably the portion of the catheter 8 that is placed within the lower groove 30 and below the strap 24. The connector fitting 82 allows the retainer 20 to compress the drainage branch 118 without significantly occluding the lumen within the drainage branch 116 due at least in part to the semi-rigid nature of the connector fitting 82.

The closed position, as illustrated in FIG. 8, is characterized by the strap 24 lying in contact or near contact with the base 22 so as to position the strap 24 above the lower groove 30. When in the closed position, the retainer 20 surrounds the received portion of the catheter.

The groove formed in the base 22 and the groove formed in the strap 24 generally define a channel 60 when the strap 24 is in the closed position. The groove formed in the strap 24 may have a longitudinal length that is the same, greater than, or less than the longitudinal length of the groove 30 in the base 22. Accordingly, the upper portion of an inner surface 69 of the channel 60 may be shorter or longer that the lower portion of the inner surface 69 of the channel 60 as measured in the longitudinal direction.

The channel 60 is capable of receiving a portion or length of the catheter 8 and is generally configured to house, grip and secure the affected catheter portion against at a portion of the inner surface 69 of the channel 60 in a contact area. The contact area may be disposed between the distal and proximal ends of the channel 60 and may extend beyond either end of the channel 60. The contact area may be located on the strap 24 and/or the base 22.

As illustrated in FIG. 6, the catheter is positioned along the longitudinal axis A so that the affected catheter portion which lies below the strap 24 when the strap 24 is in the closed position has generally a continuous circular cross-sectional shape along the longitudinal axis. Alternatively, the catheter 8 may be shifted in the distal or proximal directions along the longitudinal axis so that a different portion of the catheter 8 lies under the strap 24. For example, the catheter 8 may be shifted in the distal direction relative to its position illustrated in FIG. 6 so that the tapering portion of the catheter 8 located on the distal side of the Y-site 112 is located below the strap 24.

The channel 60 can have a variety of configurations, as discussed above in connection with the grooves in order to accommodate a particular medical article. In the illustrated embodiment, the channel 60 has generally truncated circular cross-sectional shapes at its proximal end 62 and distal end 64. The channel 60 may smoothly taper in cross-sectional size from a smaller proximal end 62 to a larger distal end 64. For example, the channel 60 may generally have a truncated V-shape that corresponds to a tapering portion of the catheter 8 retained by the securement device.

In the embodiment illustrated in FIGS. 1-8, the sides of the channel 60 are generally straight and parallel with each other. The walls of the channel 60 (and, thus, the grooves of the strap and base), however, need not be straight. For example, the wall of the base groove 30 can have a convex section that narrows the portion of the channel 60 so as to correspond in shape to the shape of the received portion of the drainage branch 116 of the catheter. This channel shape furthers retention of the catheter within the channel 60 to inhibit catheter movement through the channel, as discussed below.

Although the channel 60 can take the form of various shapes depending upon its application (i.e., depending upon a shape of the retained portion of the medical article for which the retainer is designed to be used), the channel 60 does have a sufficient length in the longitudinal direction to stabilize the catheter, rather than act as a fulcrum for the catheter, as mentioned above. That is, the retainer receives a sufficient length of the catheter to inhibit movement of the catheter in the lateral, longitudinal and transverse direction (i.e., to inhibit yaw, pitch and axial movement of the catheter), without kinking the catheter. Also, the wide-mouth shape of the channel 60 at the proximal end 62 eliminates an edge or surface over which the catheter could kink.

When the strap 24 is closed, a section of the catheter 8 is captured within the retainer 20. Thus, the retainer 20 at least restricts, if not prevents, lateral and transverse movement of the retained section of the catheter 8.

Inhibiting movement of the catheter 8 in the longitudinal direction when the catheter 8 is secured within the channel 60 is desirably accomplished by one or more retention mechanisms associated with the contact area of the channel 60. One such retention mechanism involves the shape of the channel 60 itself. The interaction between the shape of the channel 60 and a corresponding shape of the drainage branch 116 inhibits proximal longitudinal movement. As best understood from FIG. 6, the proximal end 62 and the distal end 64 of the channel 60 receive the drainage branch 116 of the catheter 8.

The interaction between the contact area on the inner surface 69 of the retainer channel 60 and the drainage branch 116 creates friction to inhibit longitudinal movement through the channel 60. The degree of interference between the catheter 8 and the retainer 20, however, cannot be so great as to significantly occlude the catheter 8.

Another retention mechanism to inhibit axial movement of the catheter 8 involves one or more friction ridges 70 located on the contact area on the inner surface 69. In the illustrated embodiment, depicted by FIG. 6, the ridges 70 are integrally formed with the base 22 and project into the channel 60. Because the illustrated embodiment also includes securement barbs, which will be described below, the friction ridges 70 are illustrated in phantom to convey that the ridges 70 can be used together with or in the alternative to the securement barbs.

The ridges 70 are desirably of smooth solid construction; however, they can be of hollow construction. The ridges 70 in the illustrated embodiment have generally triangular cross-sectional shapes and angle toward one or both ends of the channel 60. The ridges 70, however, can have other cross-sectional shapes which would interfere with axial movement of the catheter 8 through the channel 60.

Each of the ridges 70 desirably has a front wall or leading edge that forms an angle of less than 90 degrees as measured between the front wall and the inner surface 69. The ridges 70 slightly protrude into the channel 60, desirably at a transverse distance of between 0.1 to 10 mm for the given application. The ridges 70 also lie generally normal to a longitudinal axis through the channel 60.

When so arranged, the friction ridges 70 gently, but securely bite or press into an outer surface of the drainage branch 116. Such contact does not occlude or otherwise meaningfully impair fluid flow in the catheter lumen because of the compliant nature of the catheter body material and because of the degree to which the ridges 70 bite into the catheter body. Occlusion is further inhibited with the insertion of the connector fitting 82 into the drainage branch 116. This degree of contact, however, coupled with the angular orientation of the ridges inhibits movement of the catheter 8, especially in a direction opposite of that in which the ridges are angled.

Figure 12:
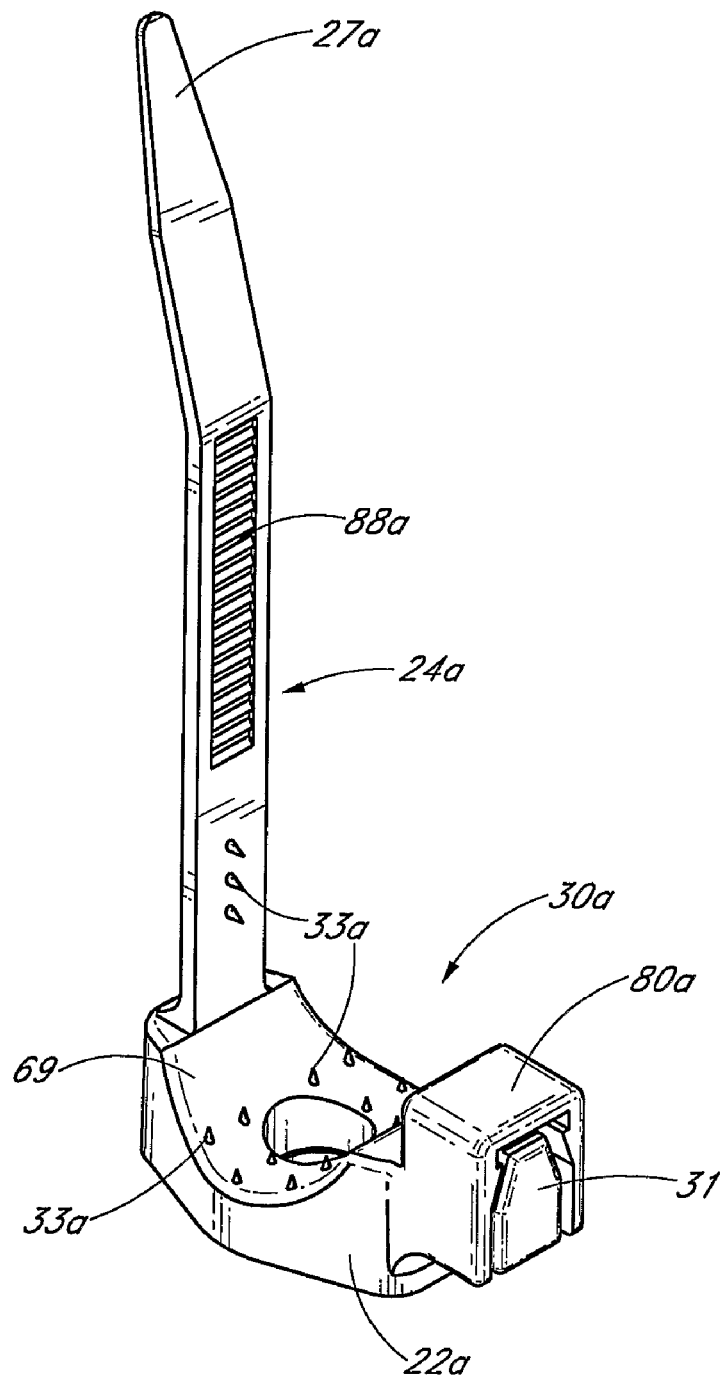
FIG. 12 is a perspective view of the retainer from FIG. 9 with the strap in an open position.

Another possible retention mechanism to inhibit axial movement of the catheter 8 relative to the retainer 20 involves one or more securement barbs 33. Exemplary securement barbs 33 are illustrated in FIG. 12. The securement barbs can be used to retain the catheter in the longitudinal direction. In certain embodiments, each barb 33 has a generally conical shape with a blunt tip. The barb 33 may extend into the channel 60 by an amount ranging between about 0.1 mm and about 3 mm.

The securement barbs 33 may be arranged within the channel 60 to cooperate with one another. The barbs 33 advantageously are arranged within the same general lateral plane (i.e., a plane defined by the lateral and transverse axes), and are spaced apart from one another. In addition, the barbs 33 desirably are spaced on generally opposite contact areas on the inner surface 69 of the channel 60 in a staggered arrangement. That is, the position of the barbs 33 alternate between the strap surface and the base surface in the lateral direction. The resulting overlapping pattern of the barbs 33 securely holds the catheter 8 without imparting torque to the catheter 8 if pulled in a longitudinal direction.

Another possible retention mechanism to inhibit axial movement of the catheter 8 relative to the retainer 20 involves an adhesive spot. An adhesive spot may be advantageously disposed upon the inside of the strap 24 within the upper groove or on the base 22 within the lower groove 30. This adhesive spot may take the form of a glue dot. Such glue dots are desirably formed of a material which exhibits high resistance to shear and which can be peeled off of the catheter without leaving a residue. Such an adhesive is sold by All-Pak Inc. of New Berlin, Wis. as part number GD-06 "Super High Tack Glue Dot." Multiple glue dots may be used, or a single glue dot may be disposed on only one side of the channel 60 of the retainer 20. It is not necessary for multiple glue dots to be used; a single glue dot disposed upon either the strap 24 or base groove 30 may advantageously be used to provide greater frictional and/or transverse forces between the retainer 20 and the catheter 8.

Furthermore, the adhesive spot need not be a single point of adhesive. In certain embodiments, the adhesive spot is a region composed of an elastic and compressively deformable material such Kraton polymer compounds. Such a compound includes Dynaflex G2706 available from GLS Corporation, as well as other thermoplastic elastomers or silicone or urethane epoxies.

This region also need not be round. In certain embodiments, a large region of the surface of the channel 60 may be covered with a suitable material, such as Kraton. For instance, the entire surface of the lower groove 30 might be covered with a thin layer of adhesive to advantageously provide additional traction and transverse bias between the catheter and retainer.

Other means of producing an appropriate adhesive spot for use with various embodiments include without limitation: treating a portion of the surface of the channel 60 chemically or electrically to adjust its surface friction or compressibility; spraying or spreading an adhesive coating onto a portion of the grooves of the retainer; attaching peel-off adhesive members to portions of the channel; injection molding regions of adhesive or compressible material, such as Kraton, to a portion of the surface of the channel; or such other means as are known in the art.

To firmly hold the drainage branch 116 within the channel 60, the retainer 20 includes interengaging structure to couple the free end 27 to the retainer 20 in the closed position. As described with reference to FIG. 1-8, the latch mechanism 80 of the interengaging structure may be fixedly attached to the base portion 25 of the strap 24. As described with reference to FIGS. 9-28, the latch mechanism 80 of the interengaging structure may be fixedly attached to the base 22 of the retainer 20. The interengaging structure may be releasable or not.

In the embodiment illustrated in FIGS. 1-8, the interengaging structure comprises a latch mechanism 80. The latch mechanism 80 may be formed with the strap 24 as a unitary piece. The latch mechanism 80 is used to secure the ends of the strap 24. In the illustrated embodiment, the interengaging structure comprises a plurality of ratchet teeth 88 or serrations and a cooperating pawl 90, each formed on opposite ends of the strap 24. The ratchet teeth 88 or serrations may be on both sides of the strap to increase holding strength. The ratchet teeth or serrations 88 are arranged on one end of the strap 24 while the pawl 90 is arranged on the other end of the strap 24. However, these components can be flip-flopped on the ends of the strap 24. Of course other interengaging structure known to one having ordinary skill in the art could be used. For example, Velcro, snaps, clips or the like could be employed to secure the strap 24.

The latch mechanism 80 includes an opening 104 that receives the end of the strap 24 having the teeth or serrations 88. The entrance of the opening 104 may include chamfer edges. The chamfer edges slope inward toward the center of the opening 104 to cause the teeth 88 to bend inward when inserting the strap into the opening 104. The opening 104 in the latch mechanism 80 may extend transversely to the plane of the base portion 25. The opening 104 is slightly taller than the thickness of the base portion 25 and is slightly wider than the width of the base portion 25 near the free end 27 so as to slidingly receive the free end 27 and the base portion 25. The opening 104 includes the pawl 90 against which the teeth 88 snap when the strap 24 is inserted through the opening 104 forming the closed position.

In operation, the ends of the strap 24 bend toward the closed position. The relatively thin strip of material forming the strap 24 allows the strap 24 to bend when finger pressure is exerted on the ends of the strap to close it. The interaction between the teeth 88 and the corresponding surface of the pawl 90 holds the strap 24 in the closed position.

For embodiments having releasable interengaging structure, the structure is simply released to remove and replace a catheter within the channel 60 of the retainer 20. The healthcare provider presses against a platform to disengage the pawl 90 from the teeth 88 and open the latch mechanism 80. The healthcare provider can then open the strap 24 and expose the inner groove 30 of the base 22.

In embodiments that are releasable, the same strap 24 may be used for an extended period of time, while permitting repeated attachment and reattachment of the catheter to the anchoring system 10. In addition, the latch mechanism 80 having a size greater than the conduit 74 ensures that the strap 24 will not be lost or misplaced when the catheter is detached from the anchoring system 10 by pulling the tooth 88 end of the strap 24. An exemplary releasable strap 24 is described in U.S. Pat. No. 4,236,280 which is hereby incorporated by reference.

For embodiments having a non-unitary strap 24 and base 22 with a non-releasable interengaging structure, the healthcare provider may remove a secured strap 24 by cutting the strap 24. A new strap 24 is then inserted through the conduit 74 and re-secured around the catheter. Advantageously, the removal and replacement of the strap 24 occurs without removing the anchor pad 12 from the patient.

As illustrated in FIGS. 7 and 8, the healthcare provider can secure a Foley catheter (or other medical article) to a patient using the above-described anchoring system (or a readily apparent modification thereof). The healthcare provider first opens the retainer 20 to expose the groove 30 on the base 22. Once opened, a drainage branch 116 portion that surrounds a connector fitting 82 can be transversely aligned over the groove 30. The catheter 8 can then be placed into the lower groove 30. Once the catheter 8 is so aligned and placed into the groove 30, the strap 24 is closed and latched, in the manner described above. The shapes of the grooves 30 ensure that the channel 60 supports the drainage branch 116 on at least diametrically opposed sides thereof along the entire retained length of the drainage branch 116. This not only enhances frictional contact between the retainer 20 and the catheter 8, but it also prevents the catheter 8 from kinking or crimping within the retainer 20 and thereby occluding the drainage branch 116.

If the retainer 20 employs projections that clamp onto or pin the catheter within the channel 60, then this engagement between the retainer and the catheter would further secure the catheter in place. If the catheter drainage branch 116 is pulled in the distal direction, the securement barbs bite into the drainage branch 116 and also oppose movement of the catheter branch 116 in this direction.

The retainer 20 thus inhibits longitudinal movement of the catheter 8 relative to the retainer, even when used with a lubricated catheter. The holding effect provided by each of the retention mechanisms, however, does not substantially occlude the drainage lumen of the catheter. The interaction of the ridges 70 and/or barbs 33 (i.e., the projection) only affects the drainage branch 116 which surrounds a rigid connector fitting 82. And although the projections bear against the catheter body, their limited bite does not significantly occlude or penetrate the drainage branch 116.

The retainer can include only one retention member or possibly several; it need not include all. In addition, any combination of the retention members (for example, an adhesive spot and securement barbs) in the retainer is also possible.

Figure 9:
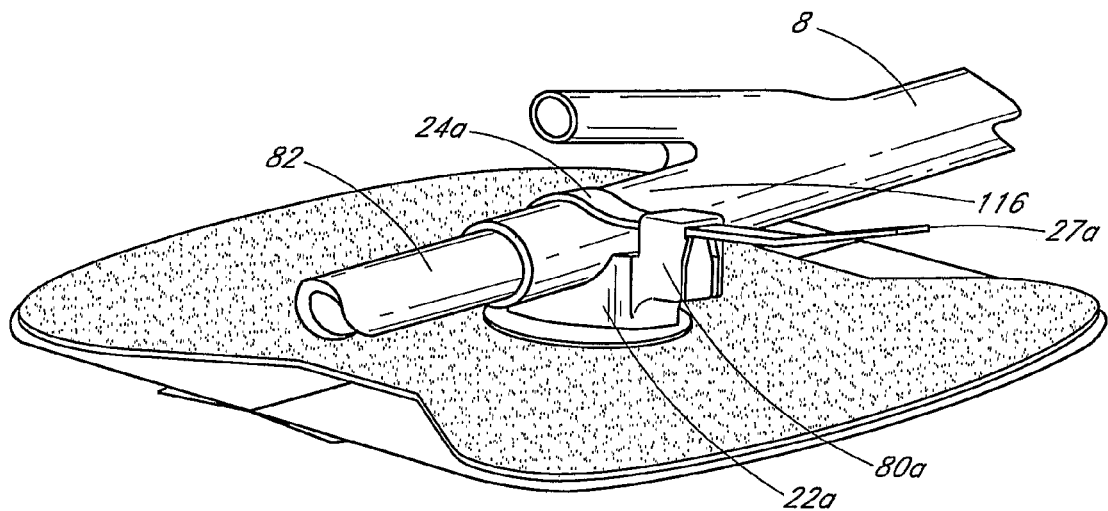
FIG. 9 is a perspective view of an anchoring system in accordance with another embodiment of the present invention, and illustrates a strap in a closed position with a catheter secured within a channel of the anchoring system.

FIG. 9 is a perspective view of another embodiment of an anchoring system having a unitary retainer 20a. The retainer 20a is similar to the retainer illustrated in FIG. 1 except that the strap 24a and latch mechanism 80a are fixedly attached to the base 22a. Features common to the anchoring systems in FIGS. 1 and 9 are identified with the same number prefix.

The suffix "a" has been added to the number prefixes illustrated in FIGS. 9 through 18.

The latch mechanism 80a is releasable allowing the strap 24a to be removed from the latch mechanism 80a. In certain embodiments, the strap 24a and retainer base 22a are manufactured together as a single piece retainer or separately manufactured and subsequently fixedly coupled together.

Figure 10:
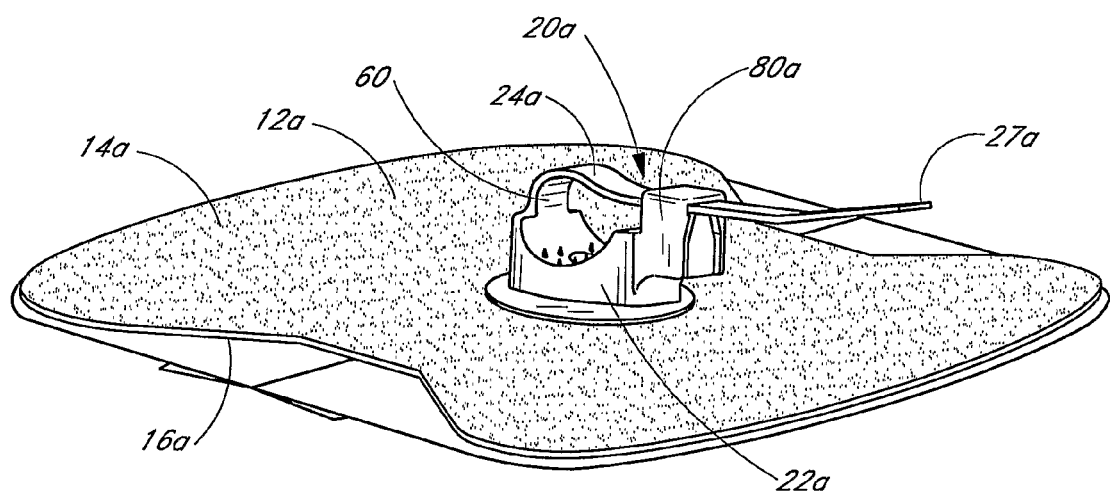
FIG. 10 is a perspective view of the anchoring system of FIG. 9, and illustrates the strap in the closed position with the catheter removed from the channel.

FIG. 10 is a perspective view of the retainer in FIG. 9 rotatably coupled to an anchor pad 12a. The catheter 8 is omitted from FIG. 10 for drawing clarity. The anchoring system includes the anchor pad 12a and the retainer 20a. The anchor pad 12a has a lower adhesive surface 16a which adheres to the skin of a patient and a roughened upper surface 14a which supports the retainer 20a. The retainer 20a is configured to accept and retain a section of a Foley catheter 8 or other medical article.

In the illustrated embodiment, the retainer comprises a base 22a, a strap 24a, and interengaging structure. The strap 24a comprises an elongated free end 27a. The strap 24a is permanently secured to a side of the retainer base 22a and moveable between open and closed positions. A plurality of teeth members or protuberances 88a are provided on the free end 27a which facilitate gripping of the free end by the healthcare provider.

The interengaging structure comprises a latch mechanism 80a and the protuberances 88a. The latch mechanism 80a is integrally formed with the retainer base 22a at the side opposite from the side secured to the strap 24a. The latch mechanism 80a is used to secure the free end of the strap 24a and includes a cooperating pawl 90a. The pawl 90a is adapted to cooperate with the plurality of teeth 88a on the free end 27a so as to retain the free end 27a within the latch mechanism 80a.

Figure 11:
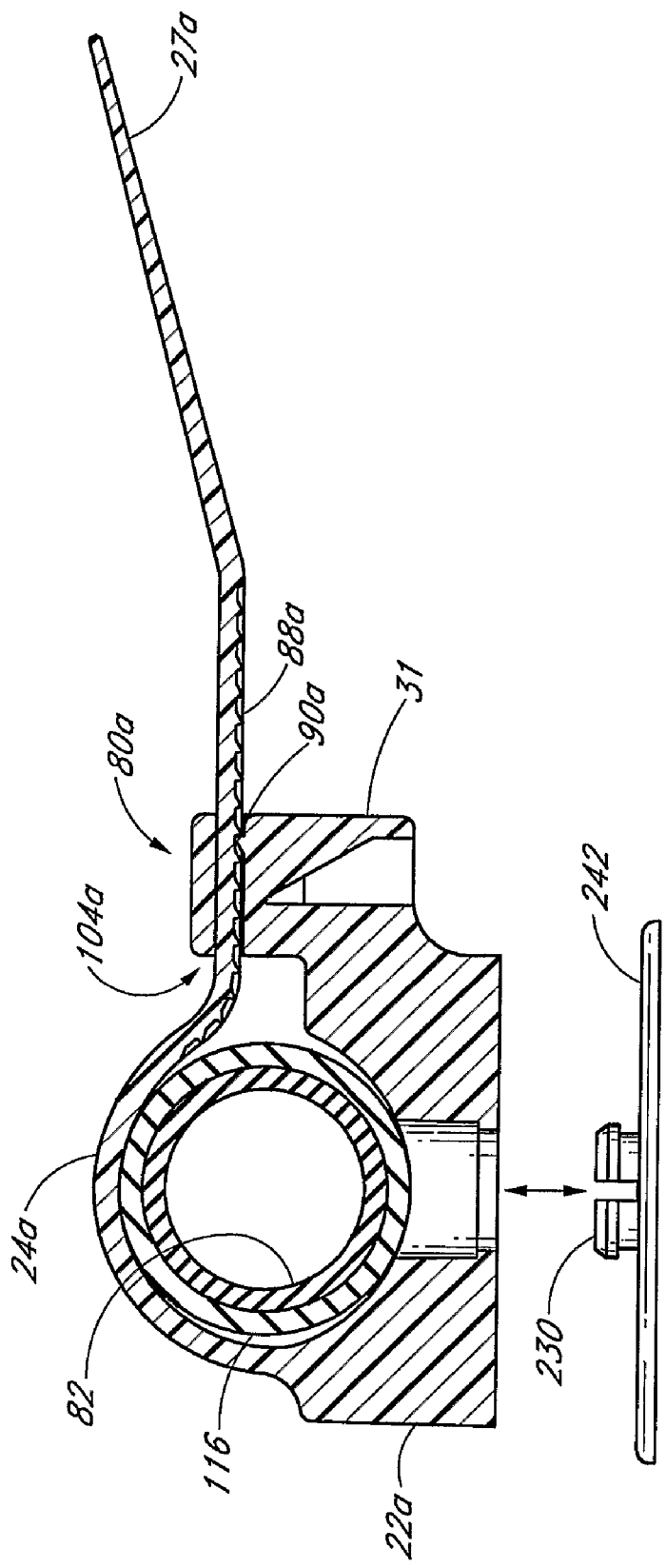
FIG. 11 is a cross-sectional view through the retainer of FIG. 9, and illustrates the strap in the closed position with the catheter secured to the retainer by interengaging structure.

FIG. 11 is a cross-sectional view of the anchoring system of FIG. 9, and illustrates the strap 24a in a closed position with the catheter 8 secured to the retainer 20 of the anchoring system by the releasable pawl 90a and teeth 88a. The healthcare provider introduces the free end 27a into an opening 104a in the latch mechanism 80a so that the complementary teeth on the strap 24a and in the latch mechanism 80a will engage to lock the strap in a selected position. The free end 27a may be tapered toward its extremity, which is rounded, so as to facilitate entry into opening 104a in the latch mechanism 80a. The latch mechanism 80a has a plurality of transversely extending teeth 90a on the same side as the gripping teeth 88a on the free end 27a.

The latch mechanism 80a includes an actuating member or latch 31 and at least one locking pawl or tooth 90a. The latch 31 is integrally molded with the latch mechanism 80a so as to be deflectable relative thereto by means of its joinder at the upper end. When the latch 31 is pressed, the locking tooth 90a is release from engagement with a selected tooth 88a on the strap 24a so as to permit the strap to move in a release direction relative to the opening 104a and thereby permit the strap 24a to be removed from the opening 104a or adjusted as desired.

Figure 13:
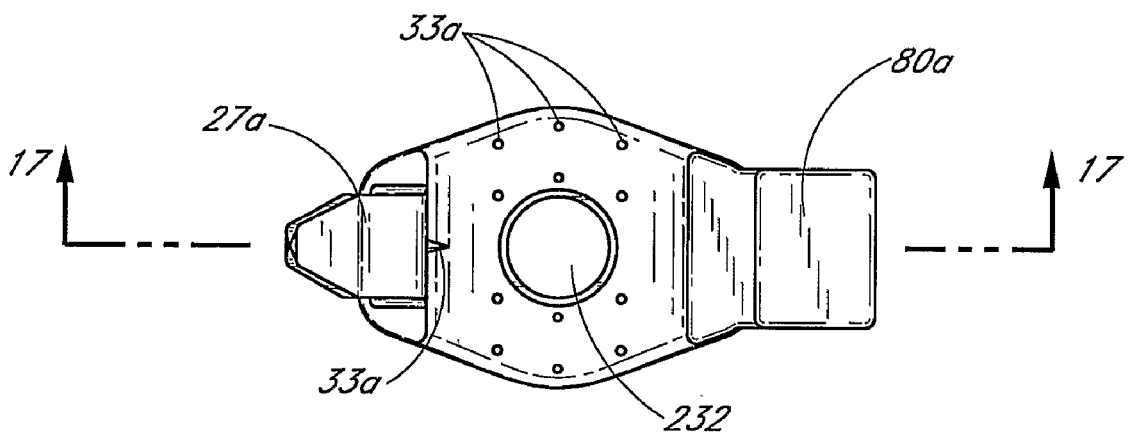
FIG. 13 is a top view of the retainer from FIG. 12 showing a plurality of barbs on a portion of the inner surface of the channel.

FIG. 12 is a perspective view of the retainer from FIG. 9 in an open position. The strap 24a illustrated in FIG. 12 extends in generally a transverse direction away from the retainer base 22a. FIG. 13 is a top view of the retainer from FIG. 12 showing a plurality of barbs 33b on portions of the contact areas on the base 22a and on the strap 24a.

Figure 14:
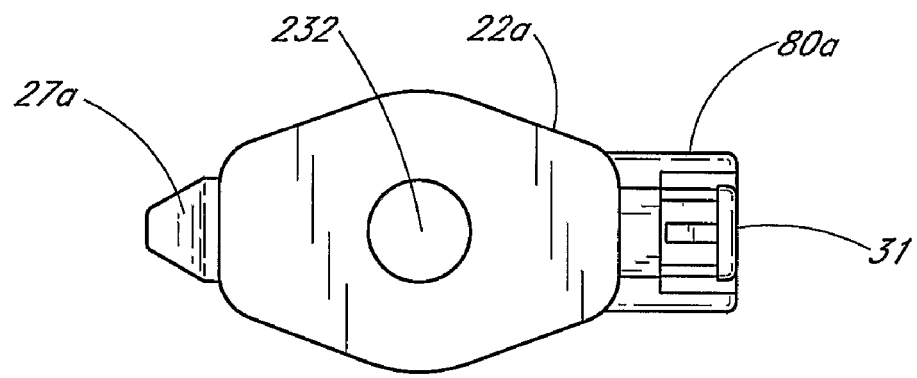
FIG. 14 is a bottom view of the retainer from FIG. 12 showing a through-hole in the base of the retainer.
Figure 15:
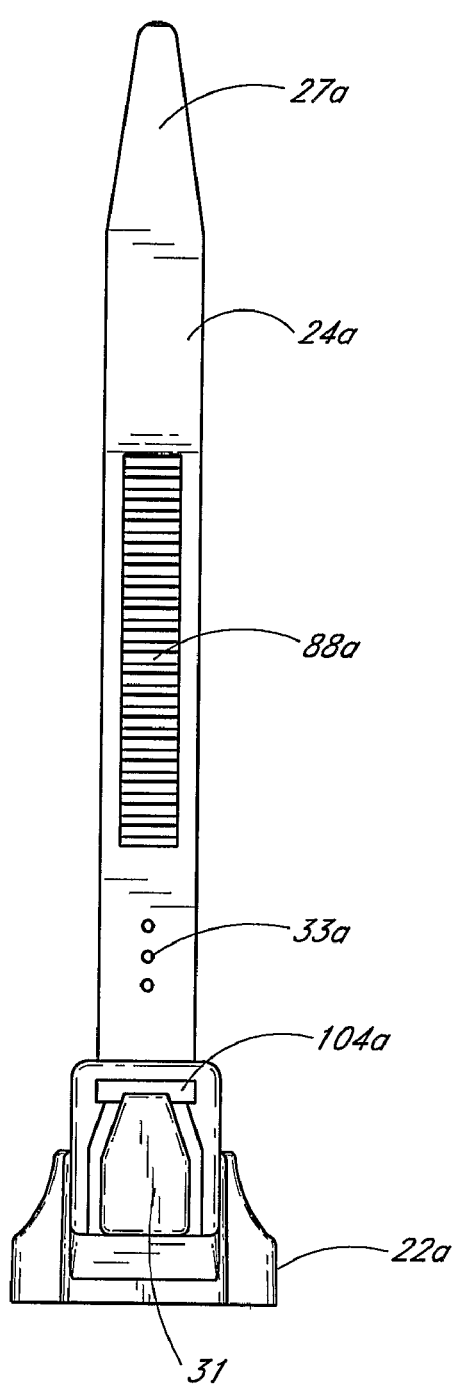
FIG. 15 is a side view of the retainer from FIG. 12 showing a plurality of ratchet teeth or serrations in the strap of the retainer.
Figure 16:
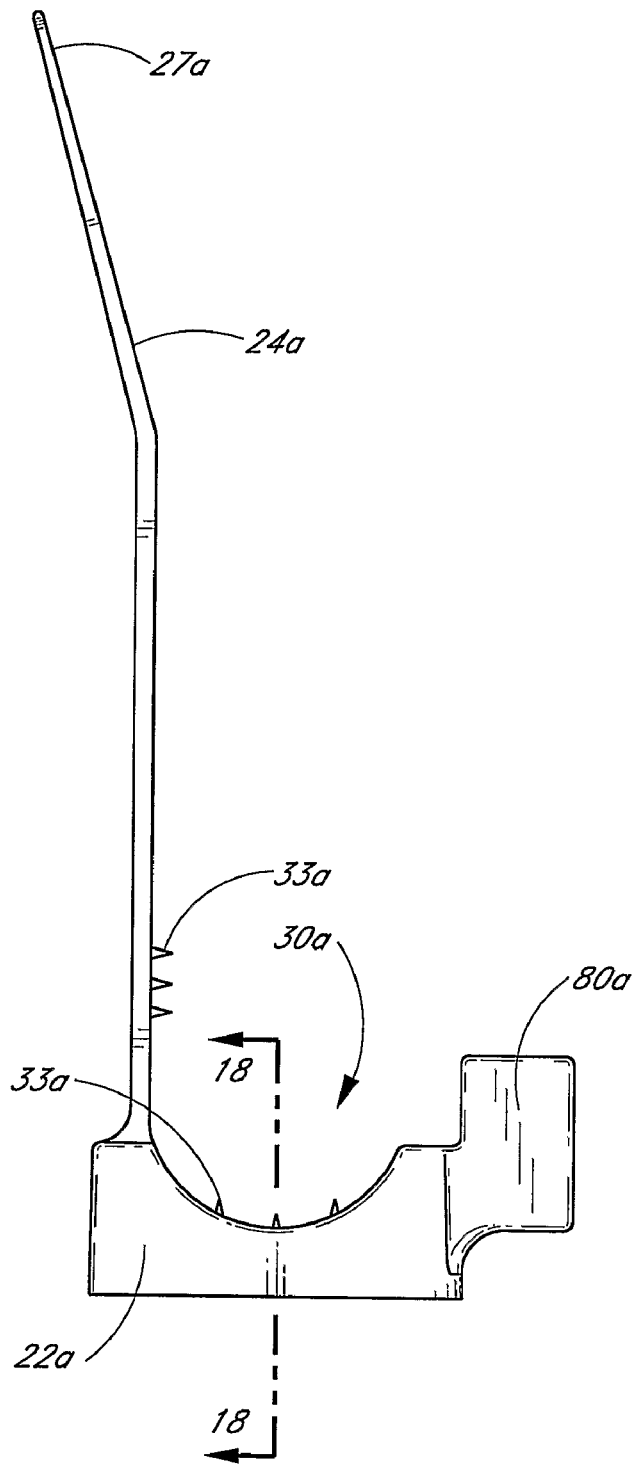
FIG. 16 is a front view of the retainer from FIG. 12 showing a base portion of the channel.
Figures 17, 18:
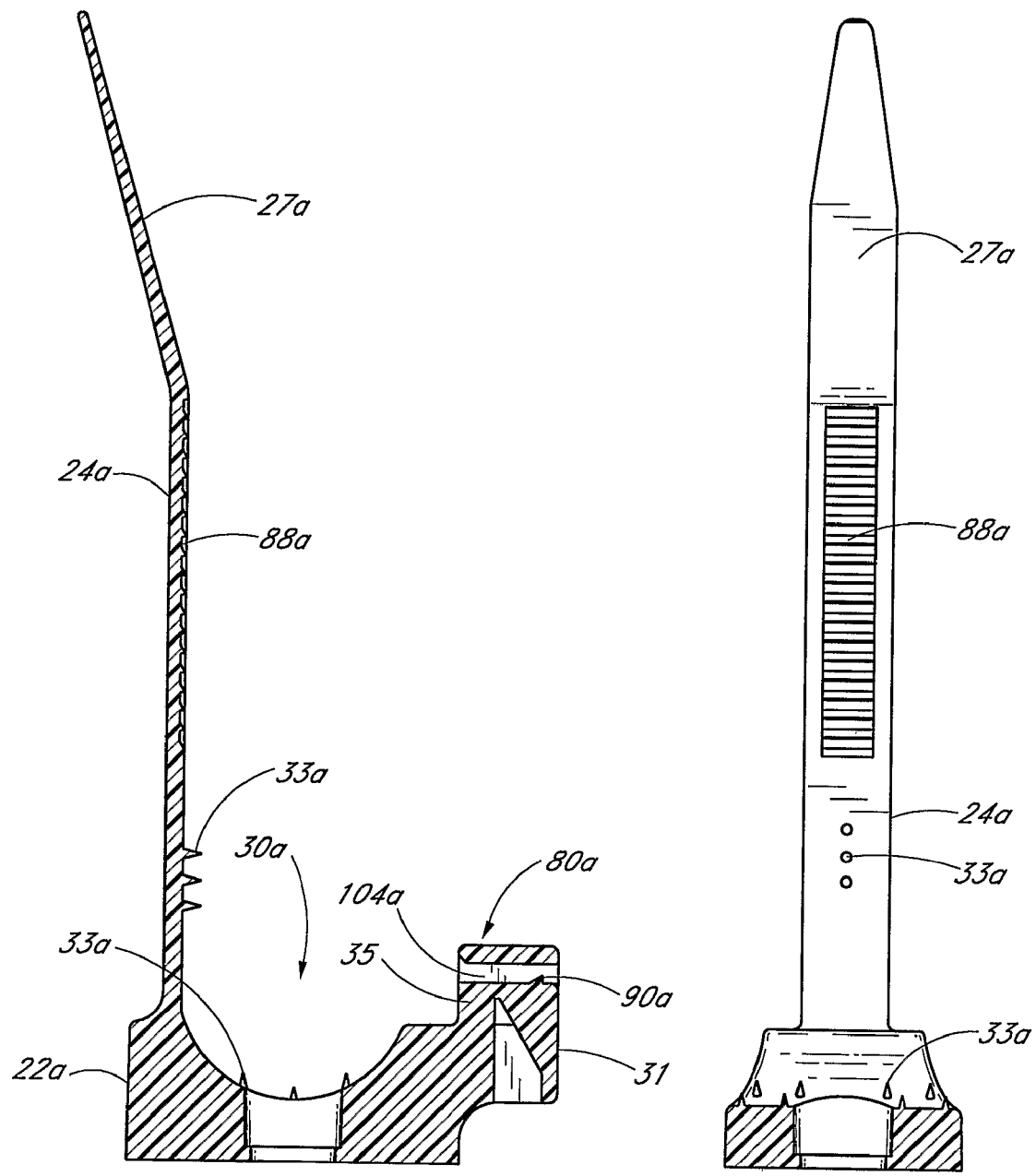
FIG. 17 is a cross-sectional view of the retainer from FIG. 12 showing a releasable latch mechanism for the strap.
FIG. 18 is a cross-sectional view taken along lines 18-18 in FIG. 16 and shows the through-hole in the base of the retainer.

FIG. 14 is a bottom view of the retainer from FIG. 12 showing a through-hole 232 in the base 22a of the retainer. FIG. 15 is a side view of the retainer 20a from FIG. 12 showing a plurality of ratchet teeth or serrations 88a in the strap 24a of the retainer. FIG. 16 is a side view of the retainer from FIG. 12 showing a groove 30a portion of the channel 60. FIG. 17 is a cross-sectional view of the retainer from FIG. 12 showing a releasable latch mechanism 80a for the strap 24a. FIG. 18 is a cross-sectional view taken along lines 18-18 in FIG. 16 and shows the through-hole 232 in the base 22a of the retainer.

With reference to FIGS. 14 and 17, the latch mechanism 80a includes an integrally formed lower bridging member 35 to which the latch 31 is joined. The bridging member 35 extends between the sides of the latch mechanism 80a. The sides of the latch mechanism 80a serve to shield the latch 31 from sidewise interference, as well as to provide additional strength to the latch mechanism 80a.

Integrally formed on the latch 31 for movement therewith and extending into the opening 104a is the locking teeth or pawl 90a. In the embodiment illustrated in FIG. 17, there is one locking tooth 90a on the inner surface of the latch 31 which defines a part of the opening 104a in the latch mechanism 80a. The locking tooth 90a is complementary to the teeth 88a on the strap 24a and extends a sufficient distance into the opening 104a to cooperate with the selected tooth 88a so as to lock the strap 24a in a selected position about the medical article.

In operation, the free end 27a is inserted into the opening 104a in the latch mechanism 80a until the strap 24a is snugly drawn about the medical article to be secured. With the strap 24a tightly drawn about the medical article 8, the complementary teeth 88a, 90a are in a locked relationship as shown in FIGS. 9 and 10. The edges of the teeth 88a normal to the strap 24a abut the edges of the teeth 90a normal to the inner surface of opening 104a. Retrogression or movement in a release direction is prevented because the abutting planar faces of the locking teeth 88a are in engagement with like cooperating surfaces on the selected cooperating teeth 90a.

Release of the locking teeth 90a from the teeth 88a on the strap 24a is attained by positive lateral force being applied upon the latch 31, so as to pivot the latch relative to the bridging portion 35 of the latch mechanism 80a. The lateral force releases the lock teeth 90a from engagement with the teeth 88a on the strap 24a. The strap 24a can now be moved in a release direction in the opening 104a so as to permit adjustment or removal of the strap 24a from the medical article 8.

Figure 19:
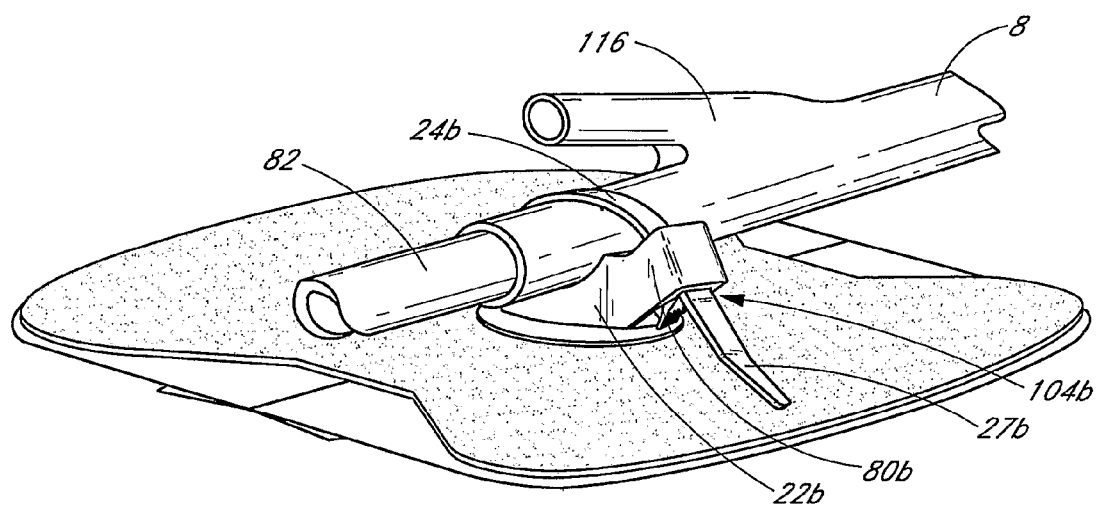
FIG. 19 is a perspective view of an anchoring system in accordance with another embodiment of the present invention, and illustrates a strap in a closed position with a catheter secured within a channel of the anchoring system.

FIG. 19 is a perspective view of another embodiment of an anchoring system having a unitary retainer 20b. The retainer 20b is similar to the retainer illustrated in FIG. 9 except that the opening 104b through the latch mechanism 80b is not parallel relative to the anchor pad 12b. The opening 104b is angled in a downward lateral direction and guides the elongated free end 27b of the strap 24b through the latch mechanism 80b. The opening 104b may be disposed such that the opening 104b is tangentially aligned with the outer circumference of the retained medical article.

Figure 22:
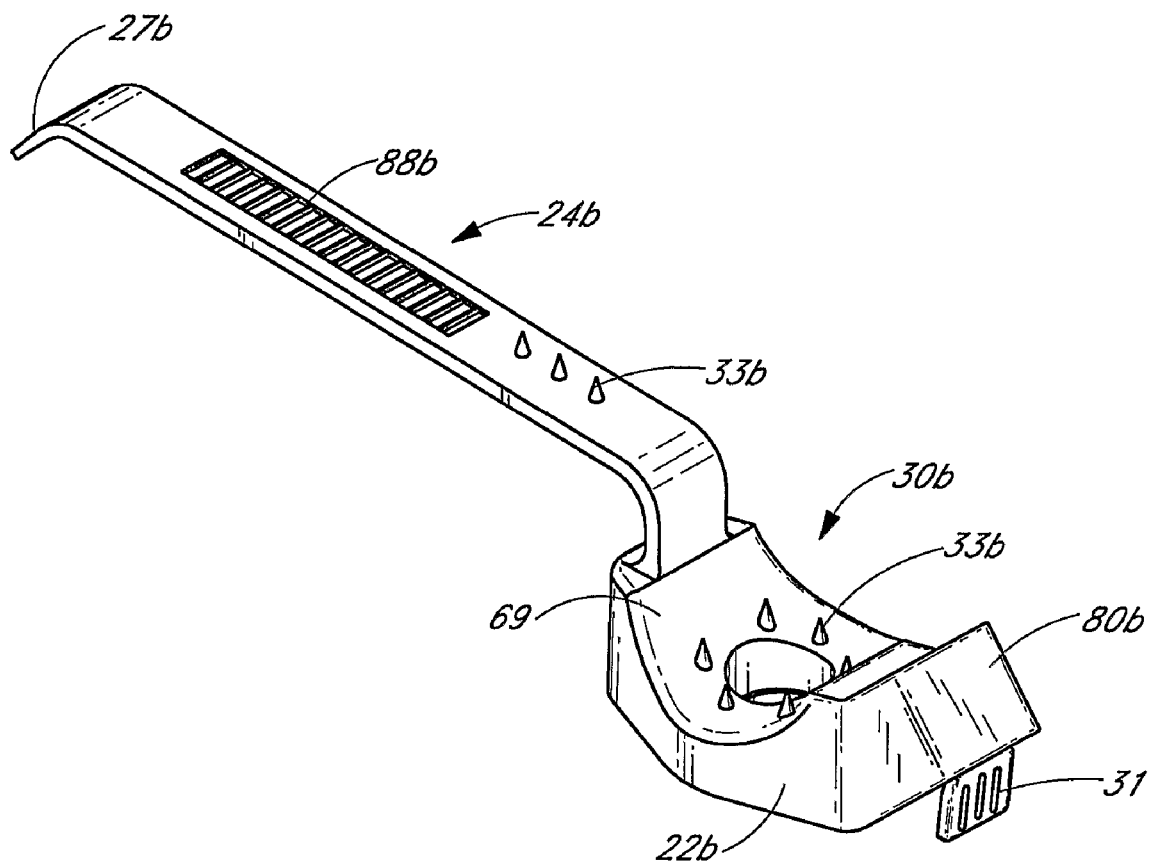
FIG. 22 is a perspective view of the retainer from FIG. 19 with the strap in an open position and extending from the retainer base in a lateral direction.

In addition, the strap 24b illustrated in FIG. 19 extends generally in a lateral direction away from the retainer base 22b and parallel to the plane of the anchor pad 12b when the strap 24b is in the open position. While only the retainer 20b is illustrated in FIG. 22, the entire anchoring system is assembled in accordance with the above-description (e.g., the anchor pad 12b is attached to the retainer 20b) and is sterilized before use. With the strap 24b extending in the lateral direction and parallel to the anchor pad 12b when the anchoring system is assembled, the anchoring system lies in a "low profile" position before use. That is, the strap 24b of the retainer 20b extends in the lateral direction to reduce the overall height of the anchoring system when in the open position, as measured in the transverse direction.

The lateral projection of the strap 24b allows the anchoring system, including the retainer 20b and the anchor pad 12b, to be easily packaged within a pouch or other sterile container. The "low profile" position of the anchoring system further allows multiple pouches to be closely packaged for storage or shipment. While lateral projection of the strap 24b is preferred, in other embodiments the strap can extend in other directions (e.g., transversely) as is illustrated, for example, in FIG. 12.

Once in the "low profile" position, the anchoring system will normally remain in the "low profile" position until use at which time the strap 24b will be secured over the catheter 8 in the opposite lateral direction and return to a "low profile" position. This position of the retainer 20b when in use reduces the risk of the anchoring system interfering with any other activities being performed by the healthcare provider.

As illustrated in FIG. 19, the angled opening 24b is more accessible for a healthcare provider to insert the elongated free end 27b into the opening 104b. The angled opening 104b further reduces bending of the strap 24b between the outer circumference of the retained medial article and the entrance to the opening 104b when inserting the free end 27b into the opening 104b. By reducing the amount of bending to the strap 24b, the strap 24b may more closely follow the outer circumference of the retained medical article and minimize gaps between the retained medical article and the strap 24b. Features common to the anchoring systems in FIGS. 9 and 19 are identified with the same number prefix. The suffix "b" replaces the suffix "a" next to the number prefixes illustrated in FIGS. 19 through 28. Thus, the detailed description for features of the retainer 20a applies with equal force to the similar features found in the retainer 20b.

Figure 20:
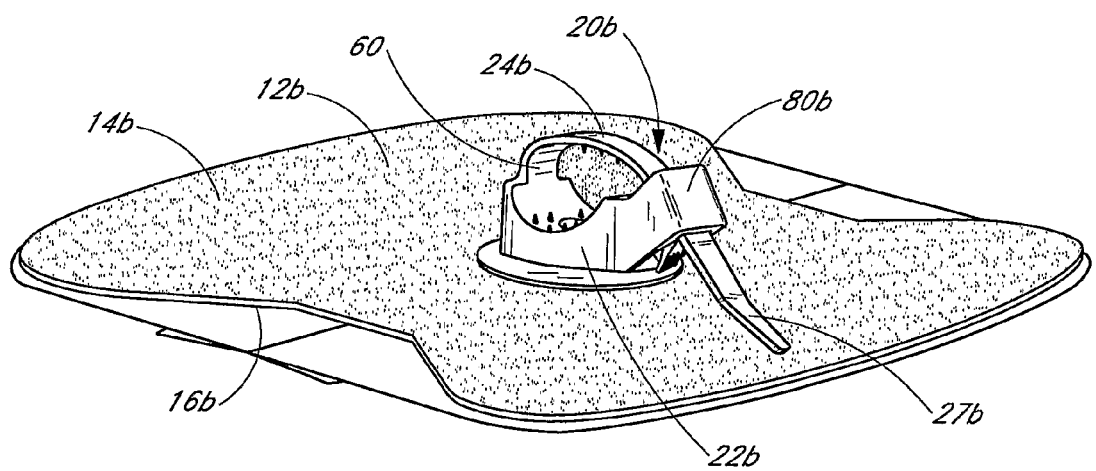
FIG. 20 is a perspective view of the anchoring system of FIG. 19, and illustrates the strap in the closed position with the catheter removed from the channel.

FIG. 20 is a perspective view of the retainer 20b in FIG. 19 rotatably coupled to an anchor pad 12b. The anchoring system includes the anchor pad 12b and the retainer 20b. The description of the anchor pad 12b in FIG. 20 is the same as the description of the anchor pad 12b in FIG. 10.

In the illustrated embodiment, the retainer 20b comprises a base 22b, a strap 24b, and interengaging structure. The strap 24b comprises an elongated free end 27b. The strap 24b is permanently secured to a side of the retainer base 22b and moveable between open and closed positions. A plurality of teeth members or protuberances 88b are provided on the free end 27b which facilitate gripping of the free end by the medical provider.

The interengaging structure comprises a latch mechanism 80b and the protuberances 88b. The latch mechanism 80b is integrally formed with the retainer base 22b at the side opposite from the side secured to the strap 24b. The latch mechanism 80b is used to secure the free end of the strap 24b and includes a cooperating pawl 90b. The pawl 90b is adapted to cooperate with a complementary tooth 88b on the free end 27b so as to retain the free end 27b within the latch mechanism 80b.

Figure 21:
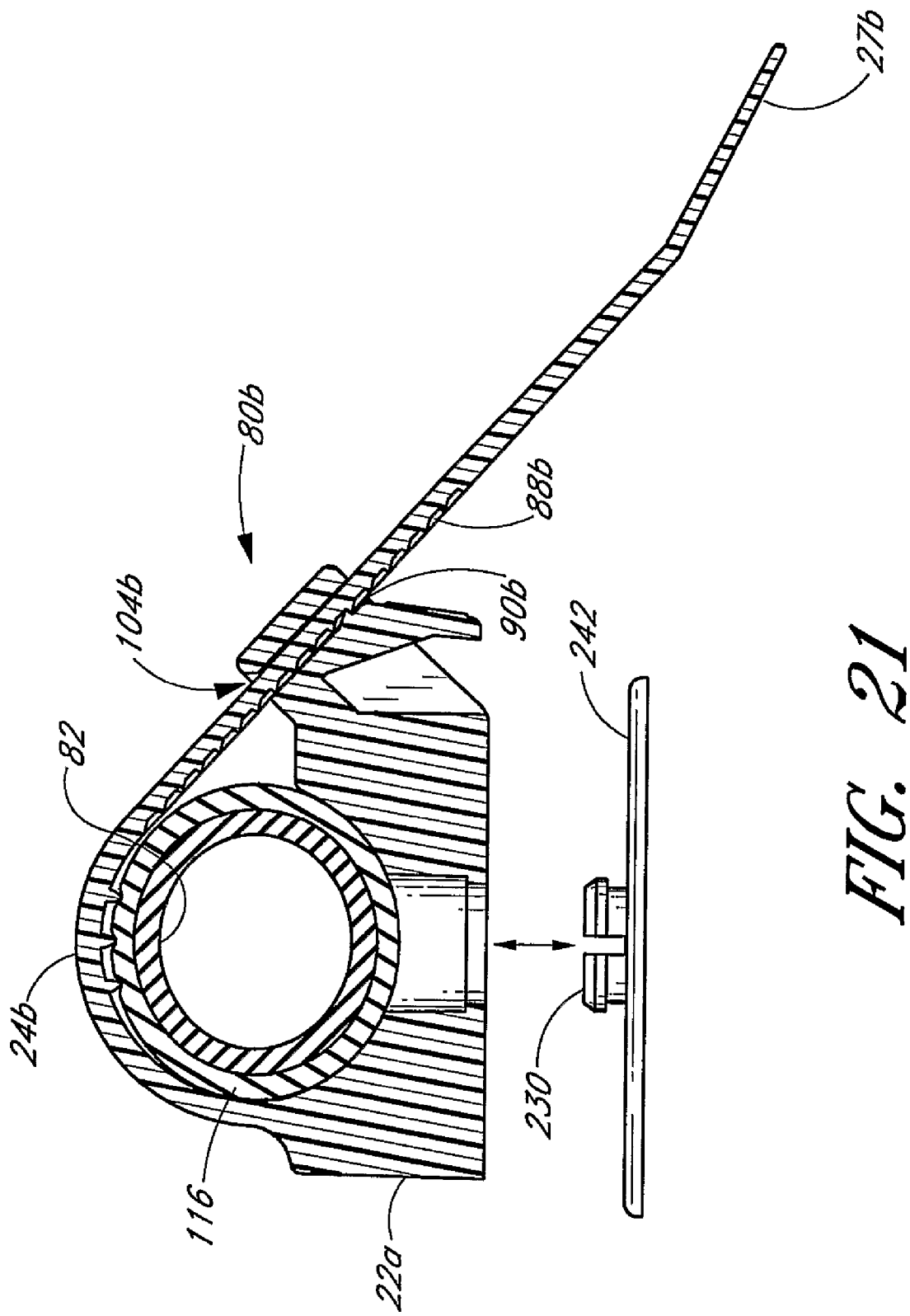
FIG. 21 is a cross-sectional view through the retainer of FIG. 19, and illustrates the strap in a closed position with the catheter secured to the retainer by interengaging structure.

FIG. 21 is a cross-sectional view of the anchoring system of FIG. 19, and illustrates the strap 24b in a closed position with the catheter 8 secured to the retainer 20b of the anchoring system by a releasable pawl 90b and teeth 88b. The healthcare provider introduces the free end 27b into an angled opening 104b in the latch mechanism 80b so that the complementary teeth on the strap 24b and in the latch mechanism 80b will engage to lock the strap in a selected position. The strap 24b is preferably inserted in a downward lateral direction through the angled opening 104b.

As illustrated in FIG. 19, the degree of accessibility to the angled opening 24b is improved for the healthcare provider to insert the strap 24b into the opening 104b. FIG. 22 is a perspective view of the retainer 20b from FIG. 19 in an open position. FIG. 23 is a top view of the retainer 20b from FIG. 22 showing a plurality of barbs 33b on portions of the contact areas on the base 22b and on the strap 24b. The description of the securement barbs 33b in FIG. 22 is the same as the description of the securement barbs 33a in FIG. 12.

Figure 25:
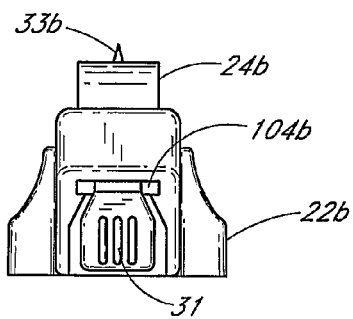
FIG. 25 is a side view of the retainer from FIG. 22.
Figure 26:
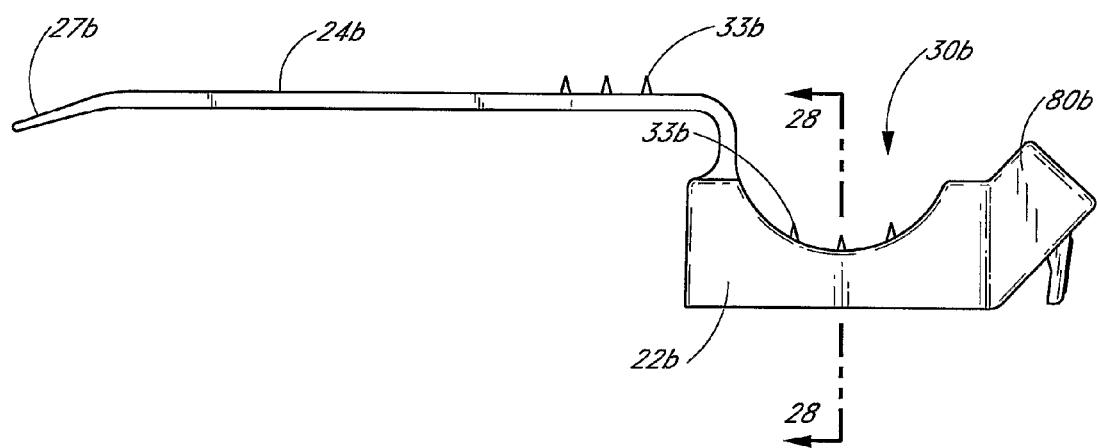
FIG. 26 is a front view of the retainer from FIG. 22 showing an angled latch mechanism.
Figure 28:
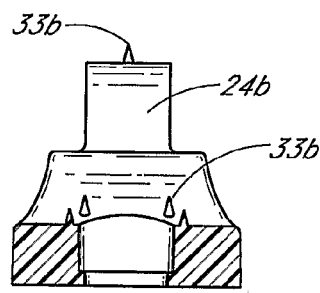
FIG. 28 is a cross-sectional view taken along lines 28-28 in FIG. 26 and shows the through-hole in the base of the retainer.
Figure 27:
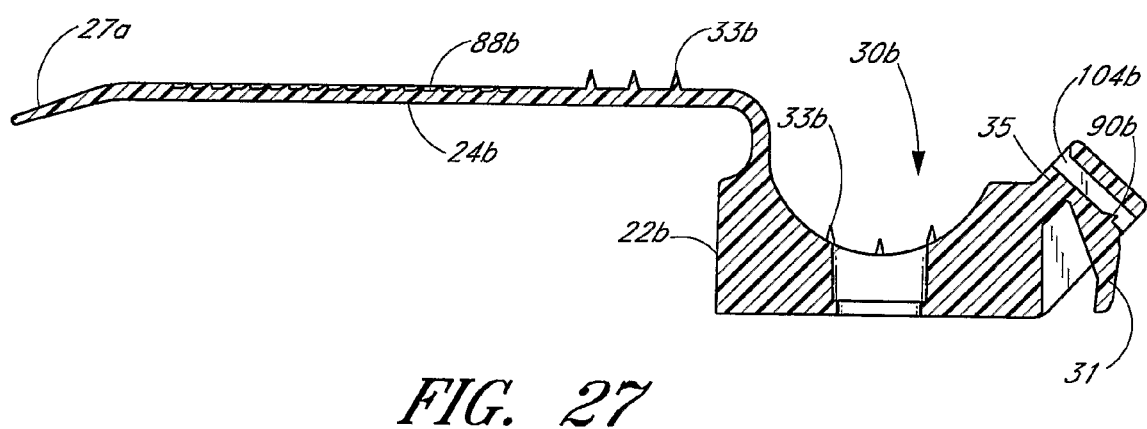
FIG. 27 is a cross-sectional view of the retainer from FIG. 22 showing an angled opening through the latch mechanism.

FIG. 24 is a bottom view of the retainer from FIG. 22 showing a through-hole 232 in the base 22b of the retainer. FIG. 25 is a side view of the retainer 20b from FIG. 22. FIG. 26 is a side view of the retainer from FIG. 22 showing the angled latch mechanism 80b. FIG. 27 is a cross-sectional view of the retainer from FIG. 22 showing the angled opening 104b through the latch mechanism 80b. FIG. 28 is a cross-sectional view taken along lines 28-28 in FIG. 26 and shows the through-hole 232 in the base 22b of the retainer.

In operation, the free end 27b is inserted in a downward transverse direction into the angled opening 104b in the latch mechanism 80b until the strap 24b is snugly drawn about the medical article to be secured. With the strap 24b tightly drawn about the medical article 8, the complementary teeth 88b, 90b are in a locked relationship as shown in FIGS. 19 and 20. The edges of the teeth 88b normal to the strap 24b abut the edges of the teeth 90b normal to the inner surface of opening 104b. Retrogression or movement in a release direction is prevented because the abutting planar faces of the locking teeth 88b are in engagement with like cooperating surfaces on the selected cooperating teeth 90b.

Release of the locking teeth 90b from the teeth 88b on the strap 24b is attained by positive lateral force being applied upon the latch 31, so as to pivot the latch relative to the bridging portion 35 of the latch mechanism 80b. The lateral force releases the lock teeth 90b from engagement with the teeth 88b on the strap 24b. The strap 24b can now be moved in a release direction in the opening 104b so as to permit adjustment or removal of the strap 24b from the medical article 8.

As is apparent from the foregoing description the retainer is readily releasable by means of the integral latch and can be easily refastened and adjusted as desired. The present anchoring system thus provides a sterile, tight-gripping, needle- and tape-free way to anchor a medical article to a patient. The retainer thus eliminates use of tape, and if prior protocol required suturing, it also eliminates accidental needle sticks, suture-wound-site infections and scarring. In addition, the retainer can be configured to be used with any of a wide variety of catheters, tubes, wires, and other medical articles. Patient comfort is also enhanced and application time is decreased with the use of the present anchoring system.

The skilled artisan will also recognize the interchangeability of various features from different embodiments. For instance, the angular orientation of the strap illustrated in FIG. 22 can be employed with the strap illustrated in FIG. 1. The upturned lip 244 illustrated in FIG. 3 can be employed with the mounting base 242 illustrated in FIG. 21. Thus, various features of the embodiments can be combined in order to adapt the anchoring system to a particular application.

Although this invention has been described in terms of certain preferred embodiments and suggested possible modifications thereto, other embodiments and modifications apparent to those of ordinary skill in the art are also within the scope of this invention. Accordingly, the scope of the invention is intended to be defined only by the claims which follow.

What is claimed is:

1. A method of making an anchoring system, comprising:
providing an anchor pad having an upper surface and a lower surface, the lower surface including adhesive;
attaching a mounting base to the upper surface of the anchor pad, the mounting base including an integral slotted mounting post formed as a single, molded piece, the mounting post including a pedestal having a flared annular fillet at a base thereof, and a cap extending radially outward therefrom and defining a circular outer perimeter, the mounting post including a slot traversing the cap; and
coupling a retainer to the mounting base by inserting the mounting post into a through-hole of the retainer, the through-hole and the mounting post configured to permit rotation of the retainer on the mounting base, the retainer comprising a strap designed to frictionally interact with a catheter to inhibit longitudinal movement of the catheter relative to the retainer.

2. The method of making according to claim 1, wherein the catheter is included with the anchoring system, the catheter comprising a connector fitting inserted into a proximal end of a catheter tubular portion.

3. The method of making according to claim 2, wherein the catheter tubular portion is one branch of a Y-site, and wherein the connector fitting comprises a semi-rigid material.

4. The method of making according to claim 1, wherein the strap includes a latch mechanism configured to secure the strap to the retainer in a closed position.

5. The method of making according to claim 4, wherein a surface texture of the strap comprises protrusions.

6. The method of making according to claim 1, wherein the upper surface of the anchor pad comprises a roughened portion.

7. The method of making according to claim 1, wherein attaching the mounting base comprises centrally positioning the mounting base on the upper surface, the anchor pad having an outer perimeter greater than the outer perimeter of the mounting base.

8. The method of making according to claim 1, wherein the retainer includes an interengaging structure that secures the strap such that the catheter is secured to the mounting base, the interengaging structure including a latch disposed on a base of the retainer and separated from the strap.

9. The method of making according to claim 8, wherein the interengaging structure comprises a two-way, self-locking, releasable receptacle.

10. The method of making according to claim 1, wherein the retainer includes an interengaging structure that secures the strap such that the catheter is secured to the mounting base, the interengaging structure comprising a pawl which releasably fastens the strap to a base of the retainer.

11. The method of making according to claim 1, wherein coupling the retainer further includes pressing the retainer over the mounting post until the cap is received in a corresponding groove of the retainer.

12. The method of making according to claim 1, wherein the retainer includes a concave channel configured to receive the catheter.

13. The method of making according to claim 12, wherein the concave channel comprises a securement barb designed to contact the catheter.

14. The method of making according to claim 12, wherein the concave channel comprises an adhesive disposed thereon, the adhesive designed to contact the catheter.

15. The method of making according to claim 1, wherein the retainer comprises a conduit, and wherein a portion of the strap is disposed in the conduit.

16. The method of making according to claim 1, wherein coupling the retainer further includes a first portion of the cap flexing radially inward relative to a second portion of the cap.

* * * * *